US012758727B2

(12) United States Patent
Piucci, Jr. et al.

(10) Patent No.: US 12,758,727 B2
(45) Date of Patent: Oct. 13, 2026

(54) POSITIVE DISPLACEMENT VENTILATOR FOR BREATHING ASSIST

(71) Applicant: Sperry Medtech Inc., Springfield, VT (US)

(72) Inventors: Vincent A. Piucci, Jr., Oakham, MA (US); Charles R. Sperry, Chester, CT (US)

(73) Assignee: Next Breath Inc., Saco, ME (US)

( * ) Notice: Subject to any disclaimer, the term of this patent is extended or adjusted under 35 U.S.C. 154(b) by 982 days.

(21) Appl. No.: 17/845,533

(22) Filed: Jun. 21, 2022

(65) Prior Publication Data

US 2022/0401675 A1 Dec. 22, 2022

Related U.S. Application Data

(60) Provisional application No. 63/213,433, filed on Jun. 22, 2021.

(51) Int. Cl.
*A61M 16/00* (2006.01)

(52) U.S. Cl.
CPC ...... *A61M 16/024* (2017.08); *A61M 16/0072* (2013.01); *A61M 2016/0027* (2013.01)

(58) Field of Classification Search
CPC ................ A61M 16/00; A61M 16/024; A61M 16/0063; A61M 16/0057; A61M 16/0072; A61M 2205/3331; A61M 2016/003; A61M 2016/0027; A61M 2205/3334; A61M 2016/0018; A61M 2202/0208; A61M 16/1005; A61M 16/125; A61M 16/208; A61M 16/202; A61M 2205/103; A61B 5/091
See application file for complete search history.

(56) References Cited

U.S. PATENT DOCUMENTS 1,892,217 A 12/1932 Moineau
3,794,026 A 2/1974 Jacobs
4,682,591 A 7/1987 Jones
(Continued)

FOREIGN PATENT DOCUMENTS

EP 1522366 11/2007

OTHER PUBLICATIONS

International Search Report Dated Sep. 22, 2022 From Corresponding PCT Application No. PCT/US22/034306.

*Primary Examiner* — Brandy S Lee
*Assistant Examiner* — Abigayle Dale
(74) *Attorney, Agent, or Firm* — Duquette Law Group

(57) ABSTRACT

Embodiments of the innovation relate to a ventilator, comprising: a positive displacement pump having a drive motor and configured to output a predetermined volume of inspiratory gas for each rotation of an output shaft of the drive motor; at least one pressure sensor configured to measure inspiratory pressure; and a control unit having a controller comprising a memory and a processor, the control unit disposed in electrical communication with the drive motor and with the at least one pressure sensor. The controller is configured to: receive at least one of an operation signal and a pressure sensor signal, and transmit a drive motor control signal to the drive motor to adjust at least one of a rotational speed of the output shaft and a number of rotations of the output shaft based upon the at least one of the operation signal and the pressure sensor signal.

17 Claims, 13 Drawing Sheets

(56) References Cited

U.S. PATENT DOCUMENTS

| | | | | |
|---|---|---|---|---|
| 7,726,115 | B2 | 6/2010 | Murrow | |
| 8,613,608 | B2 | 12/2013 | Ree | |
| 10,350,374 | B2 | 7/2019 | Robinson | |
| 10,357,624 | B2 | 7/2019 | Van Der Staay | |
| 10,512,742 | B2 | 12/2019 | Schwaibold | |
| 10,561,811 | B2 | 2/2020 | McBride | |
| 10,589,042 | B2 | 3/2020 | Holley et al. | |
| 10,589,053 | B2 | 3/2020 | Arcilla et al. | |
| 10,596,343 | B2 | 3/2020 | Glenn et al. | |
| 10,639,442 | B2 | 5/2020 | Piracha et al. | |
| 10,975,880 | B2 | 4/2021 | Nibu et al. | |
| 2008/0196720 | A1 | 8/2008 | Kollmeyer et al. | |
| 2016/0287824 | A1* | 10/2016 | Chang | A61M 16/204 |
| 2017/0348505 | A1* | 12/2017 | Doo | A61M 11/042 |
| 2018/0221606 | A1* | 8/2018 | Brandt | A61M 16/0066 |
| 2019/0275273 | A1 | 9/2019 | Chang | |
| 2020/0114112 | A1* | 4/2020 | Macloughlin | A61M 16/0666 |
| 2020/0306472 | A1* | 10/2020 | Modi | A61M 16/0891 |
| 2020/0360635 | A1* | 11/2020 | Chaudhry | A61M 16/208 |
| 2021/0128851 | A1* | 5/2021 | Nitta | A61M 16/0066 |
| 2022/0160991 | A1* | 5/2022 | Craig | A61M 16/06 |

* cited by examiner

POSITIVE DISPLACEMENT VENTILATOR FOR BREATHING ASSIST

RELATED APPLICATIONS

This patent application claims the benefit of U.S. Provisional Application No. 63/213,433, filed on Jun. 22, 2021, entitled "Positive Volumetric Automatic Mechanical Ventilator for Breathing Assist," the contents and teachings of which are hereby incorporated by reference in their entirety.

BACKGROUND

A medical ventilator is a device that assists with breathing for a person who is having difficulty breathing or is unable to breathe on their own. There are a number of reasons that a ventilator may be needed, such as traumatic injury, disease, stroke, surgery requiring general anesthesia, pneumonia, Chronic Obstructive Pulmonary Disease (COPD), and others. The application of ventilators ranges from providing a small amount of aid to a patient that can breathe on their own, but with difficulty, to controlling the entire breathing sequence for a patient that cannot breathe on their own at all. A ventilator works by delivering a volume of air, or an air and oxygen mixture, at a low pressure into the patient's lungs, then allowing the patient to exhale on their own.

The current standard for field emergency use is the Bag Valve Mask (BVM), such as the Ambu Bag (Ambu Inc., Columbia, MD). These devices are used in emergency situations by first responders to resuscitate, for example, a non-breathing trauma victim, and to keep them breathing in transit to an emergency room. BMVs are also frequently used in hospitals as part of standard equipment found on a crash cart, in emergency rooms, or other in critical care settings.

The BVM can include a squeeze bag, a patient valve that controls the flow of air into and out of the patient, and a mask that is placed over the patient's mouth. With the mask pressed over the patient's airway, air is forced into the lungs by squeezing the bag. The bag then refills itself with air when released, allowing it to return to its original shape. The bag can be squeezed out and re-inflated rapidly and repeatedly to resuscitate the patient and provide air, even if the patient cannot breathe on their own. When the bag is released, the patient's lungs are able to contract, expiring the air. The patient valve directs the expiratory air out into the atmosphere.

With the BVM, the rescuer must manually control the timing of breaths, the amount of air passed into the lungs, and the rate at which the air flows. Performed incorrectly, BVM ventilation can accelerate hypoxia and exacerbate the airway obstruction that naturally occurs during profoundly depressed levels of consciousness. Providing too much air volume or inspiring at too fast a rate can force air into the stomach, resulting in gastric insufflation, which can lead to vomiting and subsequent airway obstruction or aspiration and can result in serious injury or death.

The BMV requires that the rescuer stays with the patient, constantly pumping the bag until the patient is transported to a facility where the BVM can replaced by an automatic ventilator. Since it is critical that the mask creates a tight seal around the patient's mouth to ensure proper ventilation, it sometimes requires two rescuers to operate. One is positioned at the crown of the patient's head to hold the mask securely in place and maintain the proper airway position, and the other grips the bag with two hands and squeezes to provide steady, regular ventilations.

In some cases, an advanced practitioner will intubate the patient with an endotracheal tube. The BVM can then be connected to the tube, rather than to the mask. Some BVMs also have the ability to connect to an oxygen cylinder in order to provide an increased amount of oxygen to the patient.

By contrast, automatic mechanical ventilators are used, for example, in Intensive Care Units (ICUs) and during surgery involving general anesthesia. Premium, or high-acuity ventilators, most commonly found in hospital ICUs, typically have a proportional solenoid valve (PSOL) gas delivery system. This design uses two solenoid valves that proportionately control the flow of air and oxygen. An on-board compressor is necessary to provide the air. Numerous pressure sensors, flow meters, automatic valves, and other sensors and controls are used to mix air and oxygen and deliver breaths to the patient. These devices are highly complex, relatively very expensive and generally require a high level of training for a practitioner to use correctly.

For both BVMs and ventilators, three values are critical to controlling the patient's breathing: the pressure within the patient's airway, or inspiratory pressure, the rate of the air flow into the patient's lungs, and the tidal volume, or total volume of air inspired in one breath. Due to the nature of inflating a lung and the interdependencies of these values, only one or two values can be accurately controlled during an inspiration. Because of this, there are two basic modes of ventilation control that are typically used: volume control and pressure control. In volume control mode, a predetermined tidal volume of air is introduced into the patient's lungs in a predetermined amount of time, and the inspiratory pressure is a result of the patient's lung compliance. In pressure control mode, the inspiratory pressure is maintained at a predetermined value for a predetermined amount of time, and the tidal volume is determined by the patient's lung compliance. There are numerous variations of these modes but in general, either volume or pressure are controlled, and the other is resultant.

Conventional mechanical ventilators are flow controlled devices. An air pump produces a substantially continuous flow of air that must be measured by a highly accurate flow meter, then controlled by flow control valves to maintain the desired air flow. The types of air pumps used in these devices can be, for example, multi-piston compressors or centrifugal pumps. In some devices, there is no onboard pumping system, using instead hospital supplied air, which is supplied under pressure and must be controlled in the same manner as an onboard pump.

Also with conventional ventilators, one or more pressure sensors measure the inspiratory pressure. In volume control mode, the ventilator's control unit calculates the required flow rate necessary to deliver a quantity of air in a predetermined time. With the compressor running, one or more automatic flow control valves operate in a fashion that maintains that flow rate using the readings from the flow meter. In pressure control mode, a pressure sensor measures the inspiratory pressure, and the control unit uses the flow control valves to vary the air flow to maintain the predetermined pressure. The control unit uses the varying readings from the flow meter to calculate the volume of air that has been pumped and determine when a predetermined tidal volume has been reached. These descriptions of the ventilator modes are simplified for the purpose of illustrating the two general approaches. In use, there are many variations and combinations of the use of pressure, flow and volume.

SUMMARY

Conventional mechanical ventilators suffer from a variety of deficiencies.

For example, conventional clinical ventilators do not have the durability or ease of operation necessary for mass casualty or first responder use. Further, in a clinical setting, they provide a great deal of control over the patient's breathing, but this adds to their complexity of use. Some high-acuity ventilators have, for example, up to two dozen preset selectable modes as well as individual selectable settings. It requires intensive training to be able to use these devices effectively.

There have been on-going efforts in the industry to produce a low cost, simplified ventilator. In general, two approaches have been taken. One approach is to cost-reduce and simplify existing high acuity technology. However, even with these simplifications, these ventilator devices are typically expensive and complex, and are not rugged enough for field use. The other approach is to automate a BVM by attaching a mechanical arm that actuates to squeeze the bag. However, these BVM devices do not provide the needed accuracy of control of the flow of air into the patient to be utilized for anything but very short-term use in an emergency situation.

In certain ventilators, oxygen can be introduced into the air flow in order increase the total oxygen content ($FiO_2$) of the inspired breath. The ratio of oxygen to air can range from 100% oxygen to 100% air. The oxygen is generally supplied under pressure, either from a hospital air supply or from a pressurized oxygen supply bottle. In conventional ventilators, mixing oxygen with air requires additional flow control circuits that can include flow meters, control valves, and/or pressure sensors, for example, adding another level of complexity to an already complex device. By contrast to conventional mechanical ventilators, embodiments of the present innovation relate to a positive displacement ventilator for breathing assist. In one arrangement, the positive displacement ventilator is configured to treat patients using invasive, noninvasive, or high flow oxygen therapy (HFOT) ventilation modes. The use of a positive displacement pump as part of a ventilator mitigates the need for flow controls and circuitry used in conventional ventilator technology. This mechanical componentry can accurately control the pressure, volume, and flow rate of air to the patient. Additionally, this approach reduces complexity which, in turn, mitigates failure modes and cost as compared to conventional devices.

The positive displacement ventilator can be configured for use as an automatic resuscitator, an emergency transport ventilator, and an ICU ventilator. It is inexpensive relative to conventional ventilators and easy to manufacture in large quantities, and can be rugged enough for battlefield, mass casualty or other emergency use, yet can be made to be sophisticated enough for ICU use.

The positive displacement ventilator can include a positive displacement pump configured to deliver inspiration gas to a recipient with precise control over both rate of flow and delivered volume. With a positive displacement pump, every actuation of the pump produces a specific and repeatable volume of air. For example, a positive displacement pump that is driven by a motor can produce a known volume of air with each rotation of the motor. This provides the ability to pump a predetermined volume of air at a predetermined flow rate by controlling the rotational speed and number of rotations of an output shaft of a drive motor. For example, if a stepper motor is used, a control unit may control the number of steps driven and the drive rate. If a servo motor is used, the control unit can read the counts produced by an encoder on the motor and use these to control the rate and volume. By utilizing a positive displacement pump, the inventive ventilator does not require the flow meters and solenoid valves that a conventional ventilator does in order to deliver inspiration gas to a patient.

The positive displacement ventilator can include two functional control components: a positive displacement pump, such as described above, and an inspiratory pressure sensor. During an inspiration, or inhale, a control unit can monitor a pressure sensor and drive the pump motor at a rotational speed that controls flow rate and for a number of rotations that controls tidal, or total inspiration volume.

In one arrangement, in a pressure control mode, a predetermined inspiratory pressure is controlled by the rotational speed of an output shaft of the motor. For example, if the inspiratory pressure becomes higher or lower than desired, an increase in rotational speed of the output shaft can pump air at a higher flow rate, resulting in increased pressure, or at a lower rate that results in decreased pressure. The drive speed can change throughout the inspiration to adjust the pressure as necessary, for example, due to lung compliance or other patient factors.

In one arrangement, in a volume control mode, the volume of air and rate of inspiration is controlled by the number of rotations and rotational speed of the pump's drive motor. For example, if an inspiration of 500 ml in one second is desired, the control unit is configured to calculate the necessary flow rate and drive the motor at that rate for the number of rotations necessary to produce the desired result. There are many variations of ventilator control modes, however all modes can be used with the control of pressure, tidal volume, and flow rate to obtain the desired results. However, the positive displacement ventilator is configured to produce these results with only two functional elements: the pressure sensor and positive displacement pump. Embodiments of the current innovation mitigates the need for flow meters, control valves and many other sensors and components that are necessary with conventional automatic ventilators.

By controlling pressure, tidal volume, and flow rate, the control unit can analyze the flow characteristics of each breath delivered to the patient (i.e., lung compliance, lung volume, expiratory rate, potential lung leaks, etc.). This information can be used to create an adaptive system that optimizes each breath according to the patient's needs. This learning system can start with baseline settings for infant or adult. With each breath, the system discerns the patient's breathing characteristics, then adjusts pressure, tidal volume, flow rate and/or inspiration rate to deliver the optimum breath to the patient.

Expandability of this ventilator from basic usability with a simplified user interface to a full-function, or high acuity, ventilator can be accomplished via the control unit. The control unit of the positive volumetric ventilator is configured to identify and controls pressure, volume, and flow rate. With control over these three attributes, the control unit can produce any type of ventilation mode. In some arrangements, advanced modes can be accessed and adjusted via a computerized deice such as a smart phone or other wireless device. Other arrangements may utilize an additional plug-in user interface or an interface that is incorporated into the unit.

It is sometimes desirable to add oxygen to the air in order to increase the percentage of oxygen being delivered to patient recipient. In some arrangements of the current innovation, a selector device, such as a rotary control valve, proportions the volume of ambient air and oxygen entering the pump for each breath to be delivered. In other arrangements, the selector device can be configured as a control valve, such as a solenoid valve, to control the mix of air and oxygen. In some arrangements, an oxygen sensor such as an oximeter or other oxygen measuring device can be located on the recipient or within the device in order to determine the percentage of oxygen in the inspired air. This information can be used by the control unit to adjust the percentage mix.

Positive displacement pumps can take many forms. Examples include piston pumps, gear pumps and gerotors, variations of screw pumps and other devices. Embodiments of the current innovation can utilize any suitable positive displacement pumping device.

Embodiments of the innovation relate to a ventilator, comprising: a positive displacement pump having a drive motor and configured to output a predetermined volume of inspiratory gas for each rotation of an output shaft of the drive motor; at least one pressure sensor configured to measure inspiratory pressure; and a control unit having a controller comprising a memory and a processor, the control unit disposed in electrical communication with the drive motor and with the at least one pressure sensor. The controller is configured to: receive at least one of an operation signal and a pressure sensor signal, and transmit a drive motor control signal to the drive motor to adjust at least one of a rotational speed of the output shaft and a number of rotations of the output shaft based upon the at least one of the operation signal and the pressure sensor signal.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

DETAILED DESCRIPTION

Embodiments of the present innovation relate to a positive displacement ventilator for breathing assist. In one arrangement, the positive displacement ventilator is configured to treat patients using invasive, noninvasive, or high flow oxygen therapy (HFOT) ventilation modes. The use of a positive displacement pump as part of ventilator mitigates the need for flow controls and circuitry used in conventional ventilator technology. This mechanical componentry can accurately control the pressure, volume, and flow rate of air to the patient. Additionally, this approach reduces complexity which, in turn, mitigates failure modes and cost as compared to conventional ventilator devices.

Figure 1:
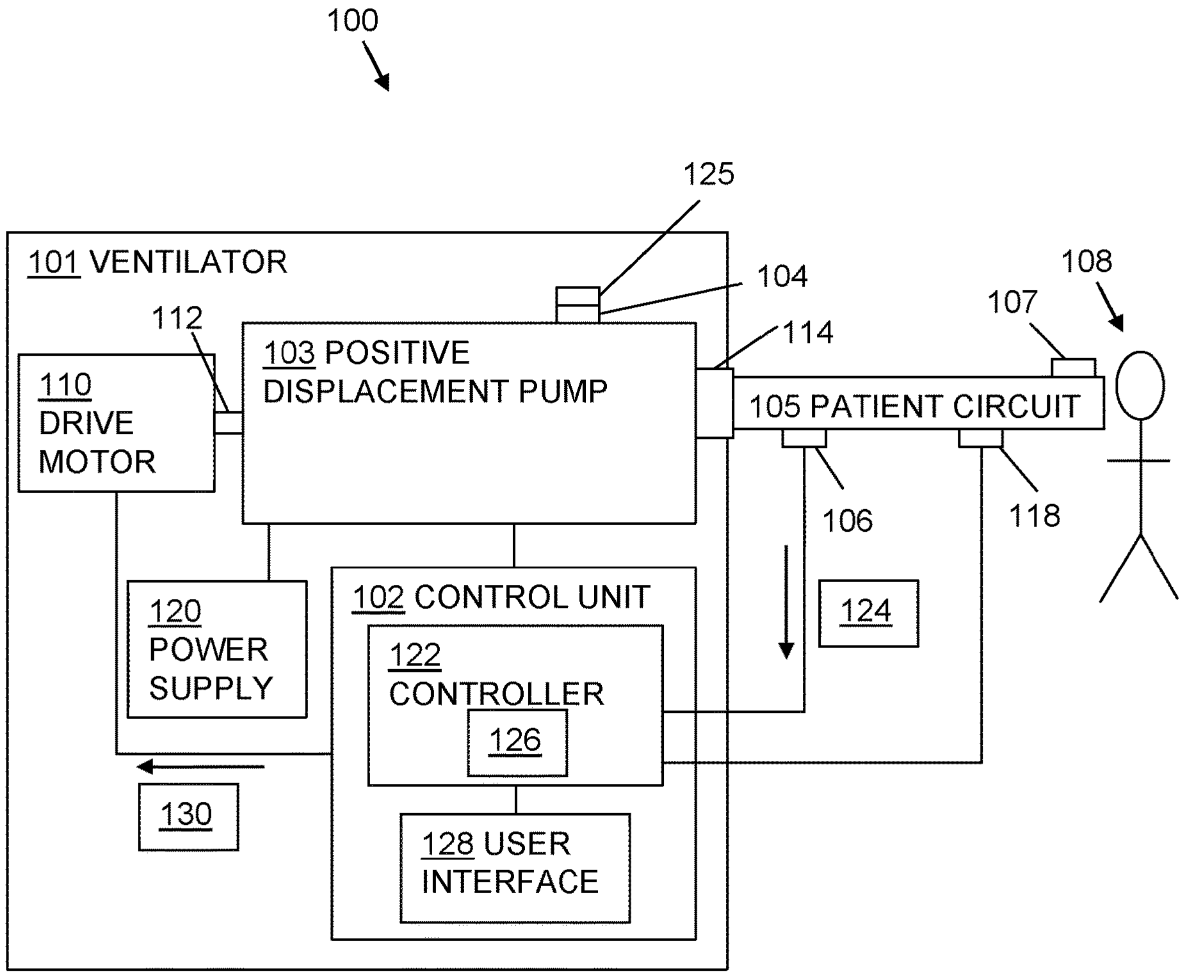
FIG. 1 illustrates a schematic representation of a positive volumetric ventilator system, according to one arrangement.

FIG. 1 illustrates a schematic representation of one arrangement of a positive displacement ventilator system 100. The ventilator system 100 can include a positive volumetric ventilator 101 having a positive displacement pump 103 disposed in fluid communication with a patient circuit 105 and with a pressure sensor 106 configured to measure inspiratory pressure, such as the pressure of the inspiration gas delivered to a recipient 108, such as a patient. In some arrangements, the pump 103 is constructed in a modular fashion which can be replaced in the positive volumetric ventilator 101. The ventilator 101 can also include a control unit 102 and a power supply 120 disposed in electrical communication with the positive displacement pump 103.

The positive displacement pump 103 is configured to supply inspiration gas, such as air and/or oxygen, to a recipient or patient 108 for inspiration. The positive displacement pump 103 includes a drive motor 110 and is configured to output a predetermined volume (e.g., a fixed, specific volume) of inspiratory gas, such as air and/or oxygen, for each rotation of an output shaft 112 of the drive motor 110. For example, air, oxygen, or a mix of the two are supplied to an inlet 104 of the pump 103 and the pump 103 delivers this as inspiratory gas to the recipient 108 via the patient circuit 105. In one arrangement, a selector device 125 is disposed in fluid communication with the positive displacement pump 103, such as via the inlet 104. The selector device 125 is configured to allow for selectable flow of air, oxygen, or a combination of air and oxygen from respective air and/or oxygen sources and into the positive displacement pump 103.

The patient circuit 105 is disposed in fluid communication with an outlet 114 of the pump 103. The patient circuit 105 can include tubing and connectors that transmit the inspiration gas to the recipient 108. In one arrangement, the pressure sensor 106 is carried by the patient circuit 105 and is configured to measure the pressure inside the patient circuit 105. During operation, the pressure sensor 106 can generate and transmit a pressure signal 124 to the control unit 102 for use in controlling the pressure inside the recipient's airway during an inspiration and in determining the recipient's condition. The positive volumetric ventilator 101 can include additional sensors, such as an oxygen sensor 118 disposed in fluid communication with the inspiratory gas and configured to measure a percentage of oxygen within inspiration gas provided by the positive displacement pump to the recipient. The sensors (e.g., pressure sensor 106, oxygen sensor 118, etc.) can be disposed in the patient circuit 105, in the pump 103, or elsewhere in the positive volumetric ventilator 101 as needed.

The patient circuit 105 can connect to the recipient 108 in a variety of ways. For example, this connection may be made through non-invasive devices such as masks or nasal canulae or invasive devices such as endotracheal tubes.

In one arrangement, the patient circuit 105 can include a patient valve 107 configured to allow inspiration gas to enter the recipient's lungs via the patient circuit 105 during an inspiration and to direct expiration air to the atmosphere as the recipient 108 exhales. The patient valve 107 can be configured with a positive expiratory end pressure (PEEP) valve, connected to the outlet of the patient valve 107, to maintain a minimum pressure inside the recipient's airway. In some arrangements, the patient valve 107 directs expiratory air through a separate airline to a valve and a pressure sensor (not shown) may be incorporated within the ventilator 101 to control PEEP. These arrangements may also utilize an expiratory air filter to clean the air exhaled by the patient.

A power supply 120 supplies the power to operate the functions of the ventilator 101. The power supply 120 can include a battery with sufficient capacity to operate the ventilator 101 for a time that is sufficient for emergency use, for example, 6 to 8 hours. The battery can be hot-swappable for easy replacement when its power has been expended. Additionally, a power cord may be included to enable the power supply 120 to be plugged into a line voltage outlet to operate the ventilator 101 for extended periods of time, such as when used in a hospital or other clinical facility and/or to recharge the battery.

The control unit 102 can include a controller 122, such a microprocessor and memory. Additionally, the control unit 102 includes a motor driver, connectors for sensors, and any other components configured to operate the automatic ventilator 101. The control unit 102 can also include components for wireless connectivity, for example, Bluetooth, WiFi or other communication devices. Communication can be used for the purposes of, for example, telemetry regarding the recipient's condition to a monitoring station. Operational conditions of the ventilator 101 may be transmitted to a local or cloud based network that may monitor the conditional of the ventilator 101 for the purposes of reporting faults that need to be addressed, or for predictive or preventive maintenance. The communication system may be used for remote control of the ventilator 101 at a central monitoring station, or through the use of a wireless device such as a smart phone, iPad, etc.

The controller 122 of the control unit 102 is configured to execute a ventilation mode engine to control the various ventilation modes that can be used with the ventilator 101. In one arrangement, the controller 122 is configured to receive and store information pertaining to the recipient 108 such as, for example, the recipient's breathing conditions. The controller can also be configured to execute an adaptive learning engine to monitor the recipient's breathing and automatically adjust ventilation parameters for any changing conditions.

The control unit 102 can also include a user interface 128. In one arrangement, the control unit 102 can include a full-function interface such as, for example, a touch screen display through which a practitioner may view current conditions and control all ventilation parameters. In one arrangement, the control unit 102 can include a simplified user interface such as, for example, a start button that begins the ventilation process, using intelligent, adaptive software that can tailor the ventilation to a recipient's conditions. The simplified interface can include limited input capability such as the selection of whether the recipient is an adult or infant, height and weight of a patient, or other parameters as desired. When supplied with a simplified interface, a practitioner may have the ability to monitor and adjust ventilation parameters through a smart phone, iPad, etc. In some arrangements, the control unit 102 is constructed in a modular fashion that can be easily and rapidly replaced in the ventilator 101.

The controller 122 of the control unit 102 is configured to receive information relating to a particular ventilator mode parameter, as well as recipient condition feedback. Based upon these parameters and feedback, the controller is configured to generate and transmit a drive signal 130 to the drive motor 110 at varying rates and duration to provide inspiration air and/or oxygen to the recipient 108 that fulfills the parameters of a particular mode. For example, the controller 122 can receive at least one of an operation signal 126, such as either provided by the user interface 128 or preconfigured in the memory of the controller, and a pressure sensor signal 124 as provided by the pressure sensor 106. Based upon the operation signal 126 and/or the pressure sensor signal 124, the controller 122 can transmit a drive motor control signal 130 to the drive motor to adjust at least one of a rotational speed of the output shaft 112 and a number of rotations of the output shaft 112 to control at least one of inspiratory gas pressure, inspiratory gas flow rate, and inspiratory gas volume.

With such a configuration the ventilator 101 mitigates the need for flow controls and circuitry used in conventional ventilator technology. This mechanical componentry can accurately control the pressure, volume, and flow rate of air to the recipient. Additionally, this approach reduces complexity which, in turn, mitigates failure modes and cost as compared to conventional ventilator devices.

Figure 2:
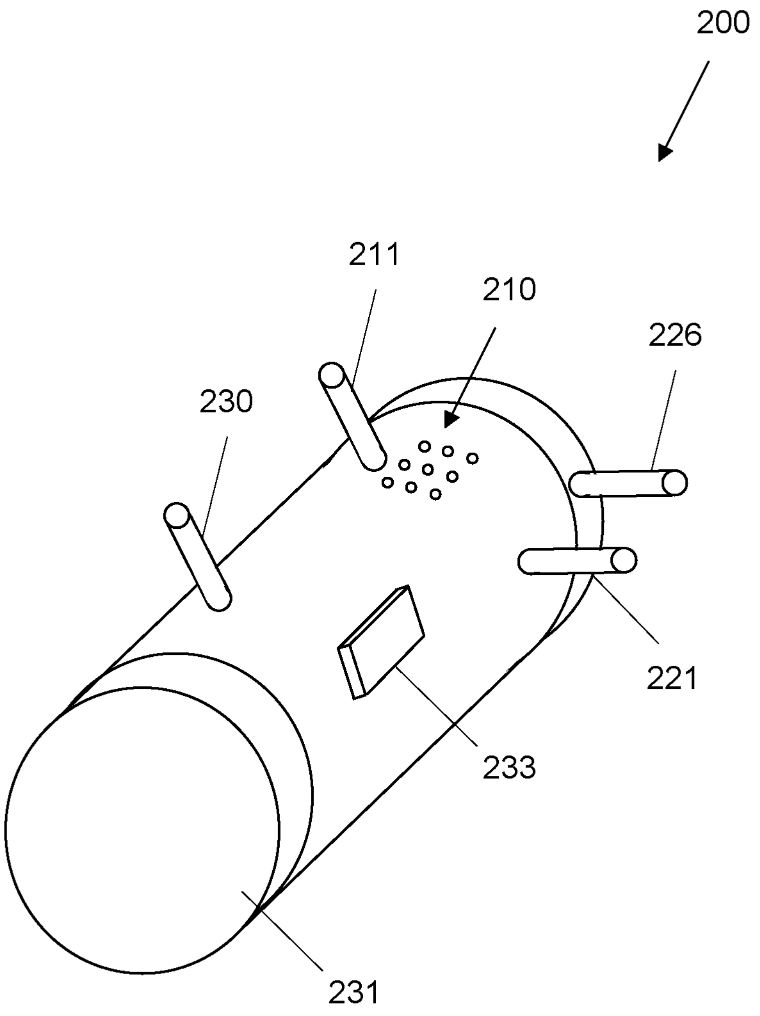
FIG. 2 illustrates an isometric view of a positive volumetric ventilator having a positive displacement pump, according to one arrangement.
Figure 3:
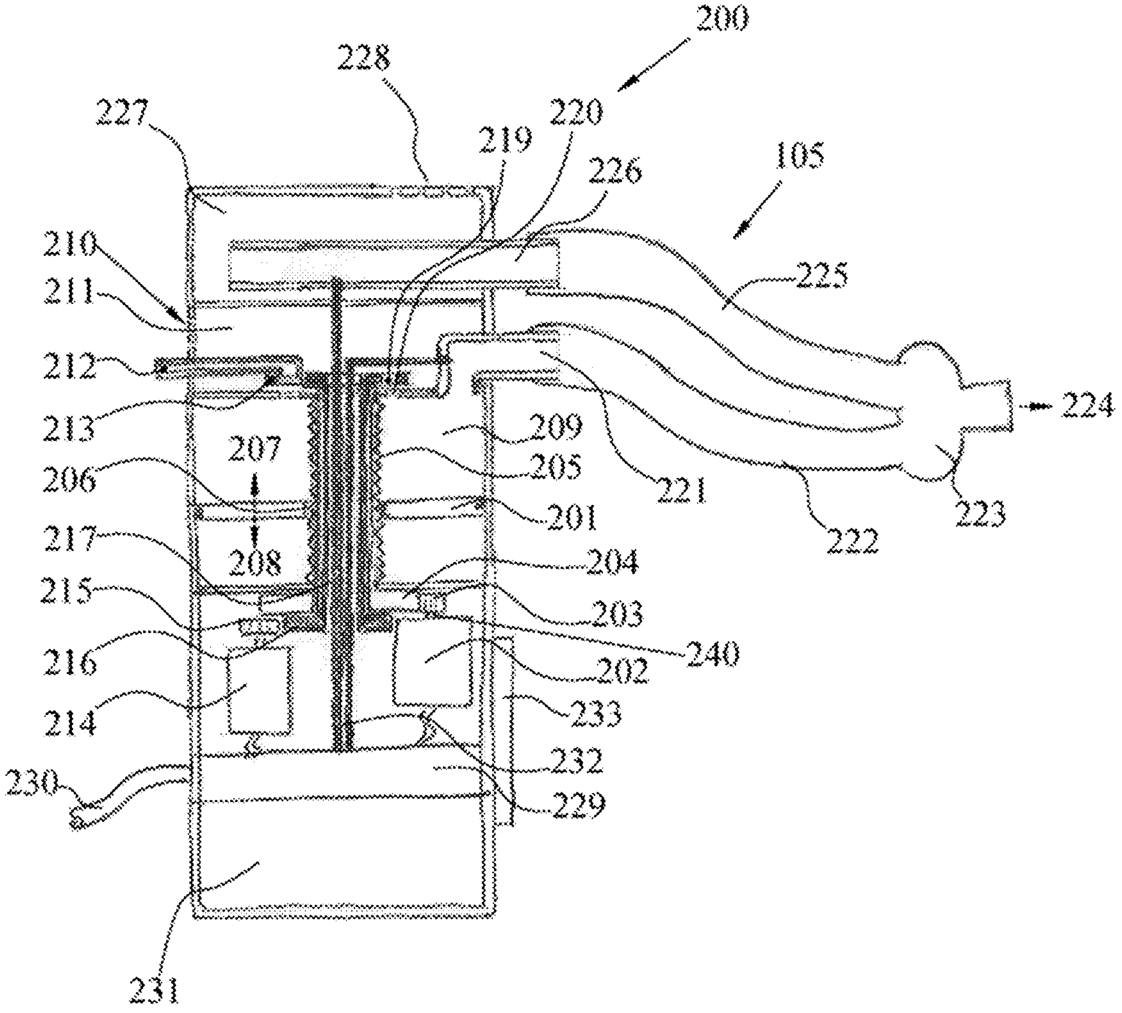
FIG. 3 illustrates a cross-sectional view of the positive volumetric ventilator of FIG. 2, according to one arrangement.

The positive displacement pump 103 can be configured in a number of ways. For example, FIGS. 2 and 3 illustrate an arrangement of a positive volumetric ventilator 200 where the positive displacement pump 103 is configured as a reciprocating pump.

The reciprocating pump of the ventilator 200 utilizes a reciprocating piston 201 as the motive force to provide the air/oxygen inspiration to the recipient. An output shaft 240 of a drive motor 202 turns a pinion gear 203 which is meshed with a driven gear 204. The driven gear 204 is attached to one end of a lead screw 205 that rotates as the control unit 229 drives the drive motor 202 in either a forward or reverse direction. The piston 201 includes an internal screw thread 206 that meshes with the threads on the lead screw 205. As the control unit 229 drives the drive motor 202 in a first direction, the rotating lead screw 205 drives the piston 201 in an upward direction 207. When the control unit 229 drives the drive motor 202 in a second, reversed direction the piston 201 translates in a downward direction 208.

As the drive motor 202 drives the piston 201 downward 208 air and/or oxygen is drawn into the enlarging volume 209 above the piston 201. It may be desirable during use to provide 100% air, 100% oxygen or any mixture in between.

Ambient air can enter the ventilator through an air inlet vent 210, into a chamber 211, then into the volume 209 above the piston 201. The chamber 211 may contain a filter medium to filter the ambient air entering the ventilator 200. Some arrangements of the ventilator 200 may be configured to allow for the attachment of a hospital air supply to the reciprocating pump. If used, oxygen can enter through an inlet 212 then into the volume 209 above the piston 201. Generally, oxygen can be supplied from a hospital oxygen supply or from an oxygen bottle.

In one arrangement, the ratio of air to oxygen that enters the piston volume 209 is controlled to a sufficient degree of accuracy. This arrangement uses a selector device, such as a rotary selector disk 213, which is a valve configured to control this mixture and to isolate the inlets 210, 212 from the piston volume 209 during an inspiration. For example, a drive motor 214 turns a pinion gear 215 that, in turn, drives a driven gear 216. The shaft of the lead screw 205 defines a longitudinal opening or hollow which is sized and shaped to accommodate a shaft 217 such that the shaft extends through the lead screw 205. During operation, as control unit 229 drives the drive motor 214, the shaft 217 rotates within the longitudinal opening of the lead screw 205. The selector disk 213 is attached to the shaft 217 and rotates with it. The rotary disk 213 defines a set of openings 219 that can be selectively aligned with the air inlet chamber 211 and the oxygen inlet 212, as well as with passageways 220 that allow the air and/or oxygen to enter the piston volume 209. The position of the selector disk 213 can be chosen to open or close any of these passageways 220. Selections may include air inlet only, oxygen inlet only and all passageways closed.

Once the piston 201 has been driven to a downward position, the piston volume 209 has been filled with the desired air/oxygen mixture. When the control unit 229, based upon the ventilation mode and specific parameters, determines that it is time for a recipient inspiration, the control unit 229 transmits a drive motor control signal 130 to the drive motor 202, causing the drive motor 202 to reverse the rotational direction of the output shaft 240, thereby driving the piston 201 in an upward direction 207. At this point, the selector disk 213 has closed all inlet passageways. The rising piston 201 now pushes the air and/or oxygen to provide an inspiration to the recipient. The inspiration gas exits the ventilator 200 through an outlet 221 and into a supply line 222 of a patient circuit 105, through a patient valve 223 and into the recipient 224 through a mask, cannula, tracheal tube, etc. The patient valve 223 is configured to allow inspiration gas to flow only to the recipient 224, and to allow expiratory gas to flow only to an expiratory line 225.

In this arrangement, the expiratory line 225 connects from the patient valve 223 back to the ventilator 200. Expiratory gas passes through the return line 225, into an inlet 226, into an expiratory chamber 227, then exhausts to atmosphere through an outlet 228. The chamber 227 may contain an expiratory filter media that can filter out contagions from the patient's expiratory gas.

The control unit 229 controls the functions of the ventilator 200 as described. A line source power attachment 230 may be included as well as a battery pack 231. Some arrangements may include a user interface 233 that may be in the form of, for example, a touch screen display.

In use, a practitioner attaches the ventilator 200 to a patient circuit 105 as shown and attaches the patient circuit 105 to the recipient using, for example, a mask, cannula, or tracheal tube. The practitioner selects a ventilation mode and initiates operation of the ventilator 200. The ventilation mode may change the mixture ratio of air and oxygen over time as the recipient is pventilated. For example, the recipient can receive 100% oxygen when ventilation begins, then over time, ambient air may be added, possibly reaching the point where 100% air is supplied.

The control unit 229 transmits a drive motor control signal 130 to the piston drive motor 202 which, in turn, begins to drive the piston 201 in a downward direction 208. For 100% oxygen, the drive motor 214 rotates the selector disk 213 into a position that allows only oxygen to enter the piston volume 209. Similarly, for 100% air the selector disk 213 is put into a position that allows only ambient air into the piston volume 209. For a mixture of air and oxygen, as the piston 201 is driven downward 208, the selector disk 213 can initially allow oxygen to enter until the piston 201 has moved to a position where a desired quantity of oxygen has entered. The selector disk 213 is then moved to a position that allows only air to enter, until the piston has reached the bottom of its travel. The piston volume 209 now contains the desired mixture of air and oxygen. The selector disk 213 now travels to a position that does not allow air or oxygen to pass through.

The selected ventilation mode will determine the operating parameters of the ventilator 200. These parameters may include, for example, length of time that the inspiration will take, length of time for expiration, inspiratory pressure to maintain, inspiratory flow rate, tidal volume, air/oxygen ratio, etc. At the desired inspiration time, the control unit 229 can transmit a drive motor control signal 130 to the drive motor 202 to cause the drive motor 202 to drive the piston 201 in an upward direction 207. This, in turn, causes the inspiration gas within the piston volume 209 to pass through the outlet 221, into the patient circuit 222, through the patient valve 223 and into the recipient.

At the end of the inspiration, the piston 201 stops upward movement 207 and begins downward movement 208, beginning the intake cycle again. The next inspiration is prepared as the recipient is exhaling.

Because the piston 201 is actuated by a screw thread, each rotation of the drive motor 202 moves the piston 201 a specific, repeatable, and accurate distance. This fixed distance within the fixed diameter of the piston cylinder displaces a known, specific volume of air. The speed at which the output shaft 240 of the drive motor 202 rotates determines the rate of flow of inspiration gas. In other words, rotating the output shaft 240 of the drive motor 202 a known number of turns produces a known inspiration volume and rotating the output shaft 240 at a known speed determines the flow rate. The control unit 229 is configured to transmit a drive motor control signal 130 to the drive motor 202 to cause the output shaft 240 to rotate at any speed and for any number of rotations within the limits of the drive motor. With no additional sensors or controls, the inspiration gas can be delivered to a recipient at any desired flow rate and volume.

The ventilator 200 is also configured to utilize one or more pressure sensors 106. In one arrangement, the sensors are located on the control unit 229 circuit board (not shown). A tube 232 passes through the longitudinal opening defined by the shaft 217 and into the outlet 221. This allows the pressure within the outlet 221 to be measured by the control unit 229. In other arrangements, this tube may continue through the patient circuit 222 or patient valve 223 to measure pressure closer to the patient. Other pressure sensor locations or arrangements are anticipated and within the scope of this innovation.

As indicated above, the ventilator 200 is configured to control inspiration flow rate and volume while sensing the patient's inspiratory pressure. As such, the positive volumetric approach of the ventilator 200 provides control over flow rate, flow volume, and inspiratory pressure. With control of these three parameters, the ventilator 200 can provide breathing ventilation of any desired ventilation mode.

Each ventilator 200 can be physically configured to provide specific inspiration gas flow parameters. In one arrangement, the diameter of the piston 201 and its length of travel can be configured to define the maximum tidal volume of each inspiration. For example, for a ventilator designed to have a maximum tidal volume of 500 ml, the piston can be dimensioned with a 10 cm diameter and a 13 cm length. Larger tidal volumes can be achieved by using a piston of larger diameter and/or longer stroke.

FIG. 3 illustrates the ventilator 200 having a piston 201 configured in a cylindrical shape and having a circular or round operational area. Piston shapes other than round may be used, such as, for example, a square or oval shape. The actual shape can be determined by piston shape, format and design preferences, for example.

Some arrangements of the ventilator can use a double sided piston system, such that there is a piston volume on either side of the piston 201. As the piston 201 travels in either direction 207, 208, it produces an inspiration on one side of the piston 201 and an intake on the other. Valves and passageways are configured to let air and oxygen enter from either end of the piston 201. As the piston 201 travels in one direction, the piston 201 pushes air from the forward side of the piston 201 and intakes air on the reverse side. In this manner, a substantially continuous flow of inspiration gas, larger in volume than the piston capacity, can be produced by reciprocating the piston 201 during an inspiration.

In some arrangements, rather than a using a reciprocating pump as described above the ventilator can include a linear, continuous output air motive pump. One such pump is a progressive cavity, or helix, pump. A progressing cavity pump is a positive displacement device that that uses a rotor and stator assembly to create temporary chambers to draw fluid into one end of the pump. These chambers move, or progress, through the pump, resulting in the fluid being discharged from the opposite end of the pump.

Figure 4:
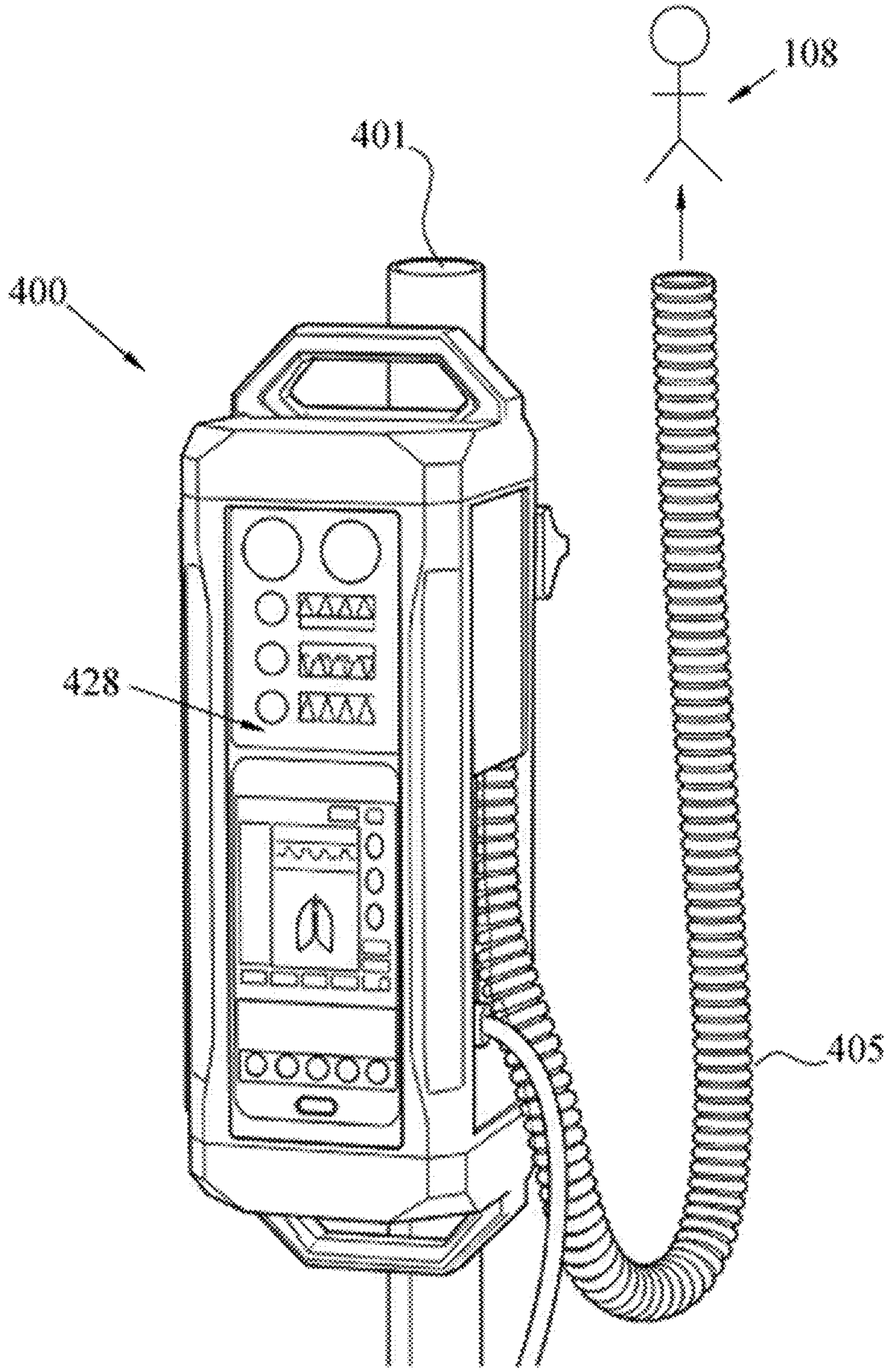
FIG. 4 illustrates an isometric view of a positive volumetric ventilator having a progressive cavity pump, according to one arrangement.
Figure 5:
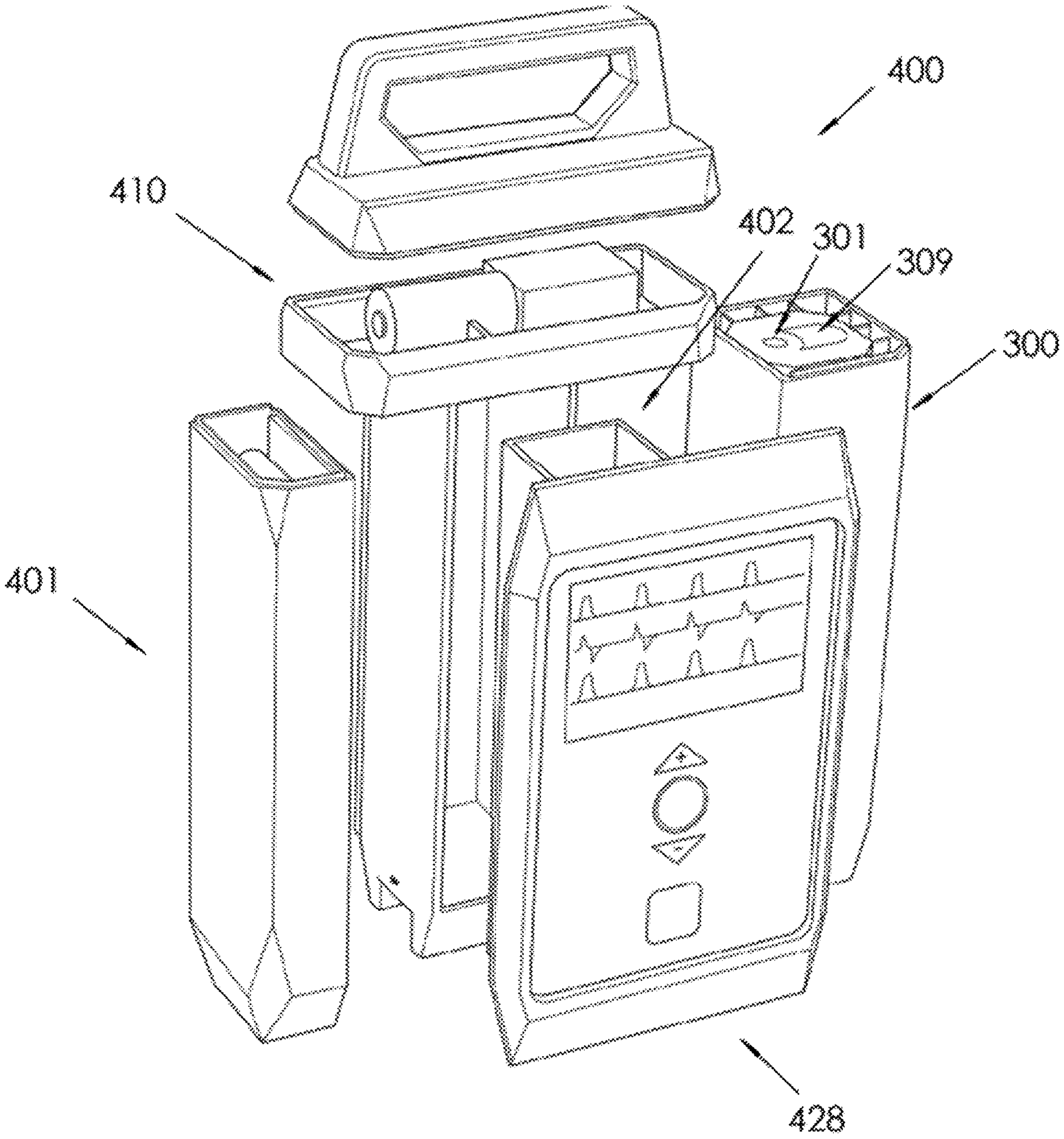
FIG. 5 illustrates an exploded view of the positive volumetric ventilator of FIG. 4, according to one arrangement.
Figure 6:
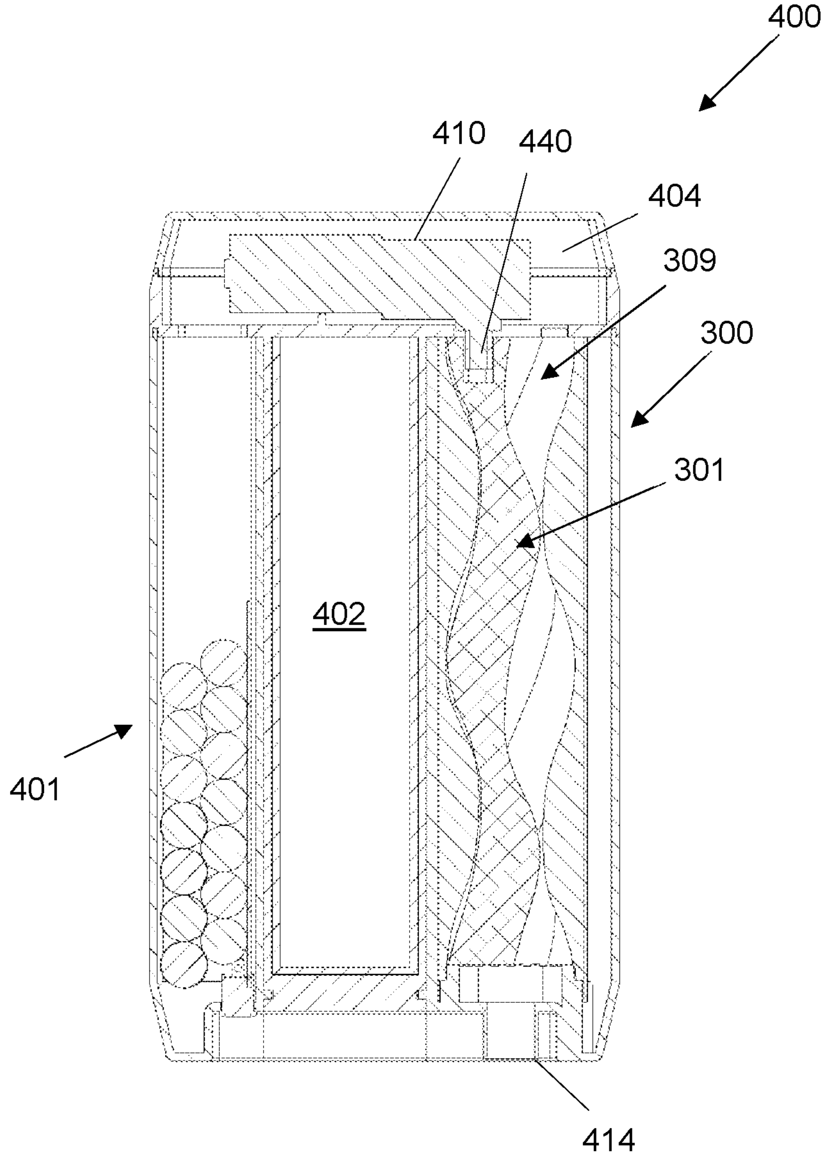
FIG. 6 illustrates a cross-sectional view of the positive volumetric ventilator of FIG. 4, according to one arrangement.

FIGS. 4-6 illustrate an example of a ventilator 400 which includes a progressive cavity pump 300, according to one arrangement. As shown, the ventilator 400 includes a control unit 402 disposed in electrical communication with a drive motor 410 and a user interface 428, as well as a power source 401. The ventilator 400 can be mounted on a pole 403 such as, for example, an IV pole. A patient circuit 405 is disposed in fluid communication with the ventilator 400 and is configured to provide inspiration gas from the ventilator 400 to a recipient 108. The user interface 428 can be configured in a variety of ways depending on the intended use of the ventilator 400 (e.g., ICU, transport, battlefield or mass casualty, high flow nasal cannula, CPAP, etc.). For example, the user interface 428 can be configured as a simple interface having an on/off and start button. In another example, such as in an ICU setting, the user interface 428 can be configured to provide the practitioner with an array of settings and outputs.

Figure 7:
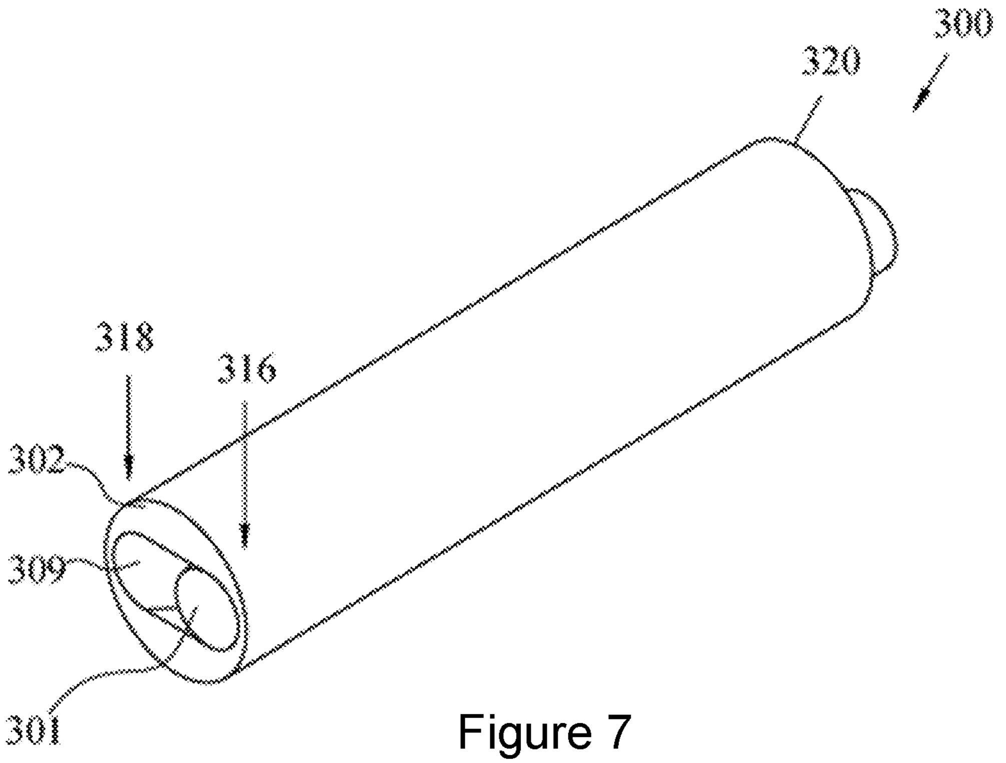
FIG. 7 illustrates an isometric view a progressive cavity pump, according to one arrangement.
Figure 8:
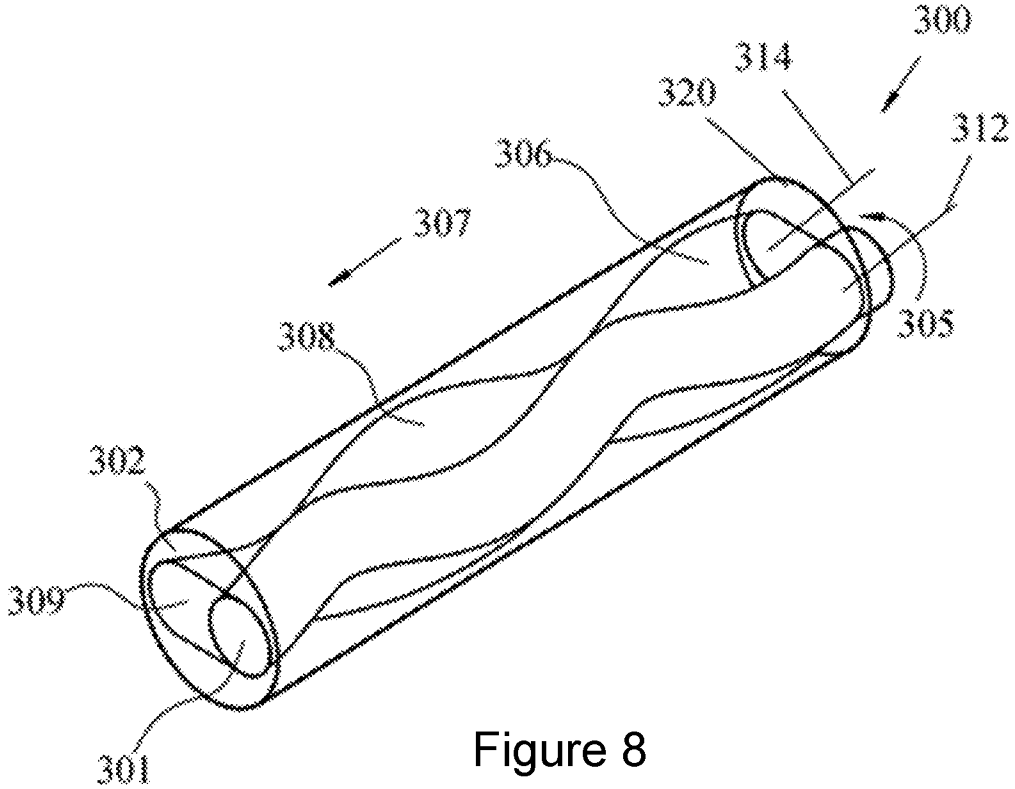
FIG. 8 illustrates an isometric sectional view the progressive cavity pump of FIG. 7, according to one arrangement.
Figure 9:
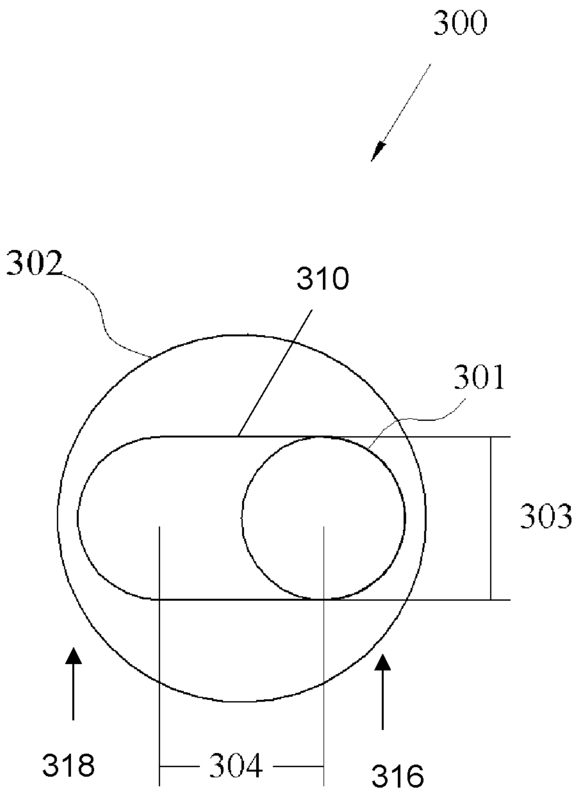
FIG. 9 illustrates an end view of the progressive cavity pump of FIG. 7, according to one arrangement.

With additional reference to FIGS. 7-9, the progressive cavity pump 300 includes a stator 302 and a rotor 301 coupled to an output shaft 440 of the drive motor 410 and configured to rotate within the stator 302. The rotor 301 and stator 302 can be configured such that the stator 302 has one helical lobe more than the rotor 301 and defines fewer helical rotations than the rotor 301. For example, the rotor 301 can include a single lobe, while the stator 302 defines two helical lobes. As such, the helix of the rotor 301 can include two rotations while the double helix of the stator 302 can include one rotation. In another example, in the case where the rotor 301 includes two lobes, the stator 302 can defines three helical lobes and, as such the rotor 301 can include three helical rotations and the stator 302 can include two rotations.

In the example of the progressive cavity pump 300 as illustrated, the rotor 301 includes a single lobe, which can be configured as a circle in cross section having a diameter 303. This circular cross section is formed into a helix of two rotations of a chosen amplitude. The eccentricity of the helix is one-half of the diameter 303 of the circular cross section. The internal bore of the stator 302 defines two circular diameters of the same dimension as the rotor diameter 303 which are separated by a distance of one diameter 304 and connected across the tangents as shown to define a straight slot 310. The internal cavity of the stator 302 is defined as a helix formed around the center point of the slot with an amplitude of one half that of the rotor 301, making one rotation. While the progressive cavity pump 300 is illustrated as having a single lobe rotor 301, such illustration is by way of example only.

As the rotor 301 rotates within the stator 302, it rotates both about a longitudinal axis 312 of the rotor 301 and also eccentrically around a center longitudinal axis 314 of the stator 302. This results in a motion in which the rotor 301 translates between a first end 316 of the slot 310 to a second end 318 of the slot 310. In the first half of one rotation, the rotor 301 moves from the first end 316 as shown in FIGS. 7-9 to the second, opposite end 318 of the slot 310. In the second half of the rotation, the rotor 301 translates from the second end 318 to its original position at the first end 316 of the slot 310.

The contact between the rotor 301 and stator 302 provides a moving cavity which forms the progressive action that propels inspiration gas through the progressive cavity pump 300. For example, during operation, as the drive motor 410 rotates the rotor 301 about longitudinal axis 305, the progressive cavity pump 300 draws air into a first end of the stator 302 and into a chamber 306 defined between the stator 302 and the rotor 301. The motion of the rotor helix relative to the stator helix moves the chamber volume 306 axially in a downstream direction 307. For example, FIG. 8 illustrates an air filled chamber 308 that has progressed partially through the progressive cavity pump 300. Once the chamber volume 306 reaches the second, opposite end 309 of the progressive cavity pump 300, the air is discharged. The direction of rotation of the stator 301 determines the direction in which the air is pumped. The chambers 306, 308 are of fixed size so that an equal amount of air is pumped for each rotation. Both flow rate and volume can be controlled by rotating the rotor 301 at a known rotational speed and for a known duration.

The size of the rotor diameter 303, helical eccentricity and number of rotations can be set according to the desired volume of inspiration gas at a desired rotational speed. For example, a progressive cavity pump 300 having a 2.54 cm diameter rotor 301 with a 1.27 cm helical eccentricity and configured to pass through two rotations with a 12.7 cm pitch can have a theoretical single rotation volume of 164 ml. As such, each rotation of the rotor 301 can pump 164 ml of air. As such, in order to produce a flow output of 500 ml/sec, drive motor 410 can rotate the rotor 301 at a rotational speed of 183 rpm and in order to produce a flow output of 1000 ml/sec drive motor 410 can rotate the rotor 301 at a rotational speed of 366 rpm. This does not take into account any inefficiency due to rotor 301 and stator 302 fit, finish, or manufacturing techniques that may cause slippage. However, the progressive cavity pump 300 is configured to deliver substantially consistent and repeatable volumes of inspiration gas, particularly at the low pressures necessary for ventilation. Accordingly, any inefficiencies can be corrected by the control unit 402. For example, control unit 402 can be configured to detect a discrepancy between a preset delivery volume value and an actual delivery volume value, as provided by the progressive cavity pump 300. In the case where the control unit 402 detects such a discrepancy, the control unit 402 can transmit an adjustment signal to the drive motor 410 to adjust the drive speed and time driven. In some arrangements, in this application, a relatively loose fit between the rotor 301 and stator 302 may provide an advantage in that it will take less motor torque to drive than a tight fitting pump and can readily operate when used in, for example, a stockpile application where the pump 300 may be stored unused for an extended period of time.

The progressive cavity pump 300 described above is by way of example only. Any suitable rotor 301 diameter, helical eccentricity, pitch length and number of helical rotations, number of lobes, as well as manufacturing material, methods and designs, including specific geometry may be employed by the current innovation.

As provided above, the rotor 301 is coupled to the output shaft 440 of the drive motor 410 and is configured to rotate within the stator 302. Since the rotor's motion is both rotative and translative within the slot 310, in one arrangement, the rotor 301 can be coupled to the output shaft 440 via a universal joint. In one arrangement, as provided in FIGS. 10 and 11, the rotor 301 can be coupled to the output shaft 440 via a drive assembly 500.

Figure 10:
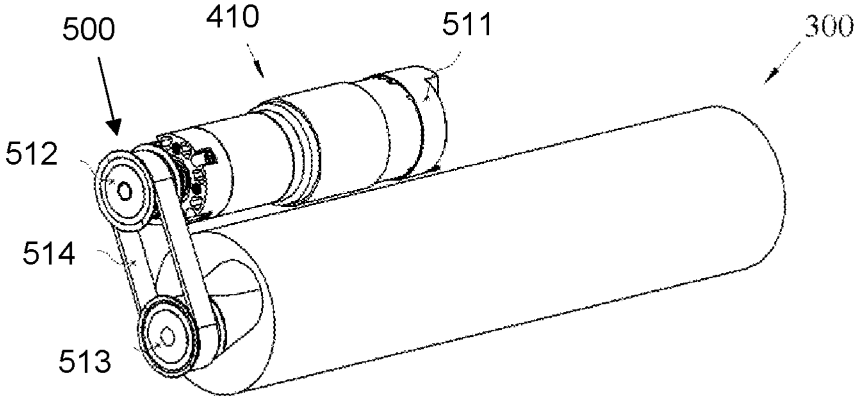
FIG. 10 illustrates a drive assembly coupling a rotor of a progressive cavity pump with a drive motor, according to one arrangement.
Figure 11:
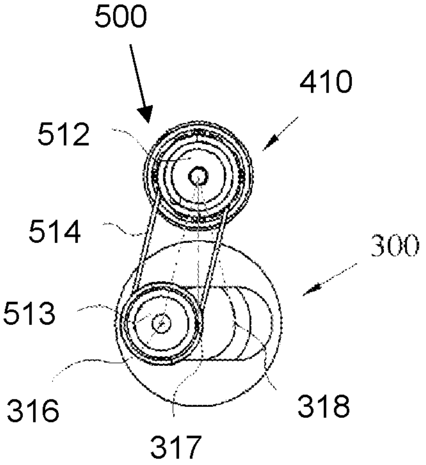
FIG. 11 illustrates an end view of the drive assembly of FIG. 10, according to one arrangement.

FIGS. 10 and 11 illustrate an arrangement of a progressive cavity pump 300 with the drive motor 410 positioned parallel and adjacent to the progressive cavity pump 300. The drive motor 410 can be configured to produce the torque and rotational speed necessary for a specific progressive cavity pump 300 arrangement. In this arrangement, an encoder 511 is disposed in operative communication with the drive motor 410 and is configured to detect and control the rotational speed and number of rotations with which the output shaft 440 of the drive motor 410 drives the progressive cavity pump 300.

The progressive cavity pump 300 further includes a drive assembly 500. In the example illustrated, a timing belt pulley 512 is attached to the output shaft 440 of the drive motor 410, and a corresponding pulley 513 is mounted onto the end of the rotor 301. A timing belt 514 connects the pulleys 512, 513 in a manner that causes the rotor 301 to rotate as the drive motor 310 is driven by the control unit 402. In one arrangement, the timing belt 514 includes a set of teeth (not shown) that mesh with a corresponding set of teeth (not shown) in the pulleys 512, 513. Such meshing mitigates the belt 514 from slipping on the pulleys 512, 513 in order to provide a positive drive. The respective size of the pulleys 512, 513 and timing belt can be determined by the specific design of the drive assembly 500.

In use, as the drive motor 410 drives the rotor 301, the end of the rotor 301 rotates within the stator 302, it rotates both about a longitudinal axis 312 of the rotor 301 and also eccentrically around a center longitudinal axis 314 of the stator 302. As such, the end of the rotor 301 translates from a position at a first end 316, through a center position 317, then to a second end 318 during the first half of the rotation. The rotor 301 then returns through the center position 317 and back to the first position 316 during the second half of the rotation. This linear translation occurs with each rotation of the rotor 301. As such the center to center distance of the pulleys 512, 513 changes through the rotation, being shortest at the center position 317 and longest at the first and second ends 316, 318. Therefore, a belt 514 that is correctly tensioned at each end 316, 318 can include some slack in the center position 316.

To mitigate the use of the belt 514 as a tensioning device, in one arrangement the drive assembly 500 can be configured to maintain tooth engagement when the rotor 301 is disposed at the center position 316 based upon the distance between the pulleys 512, 513 and the pitch of the teeth of the timing belt 514 teeth. For example, the distance between the motor pulley 512 and rotor pulley 513 can be 70 mm with the rotor 301 in the center position 317. The rotor's 301 linear travel distance from the first end 316 to the second end 318 is 25 mm. The resultant distance between the pulleys 512, 513 with the rotor 301 at the first 316 or second 318 end is 71 mm. As such, the distance between the pulleys 512, 513 changes by a distance of 1 mm during a rotation. A common tooth pitch, or distance between teeth, for a timing belt 514 is 5 mm. With the belt correctly tensioned with the rotor 301 at the first 316 or second 316 end, the slack in the belt 514 is 1 mm, which results in a change in belt 514 overall length of 2 mm. This distance relates to 40% of the length of a belt tooth. Accordingly, in the position of shortest distance, there is minimal slack in the belt 514 for the timing belt 514 to jump over a tooth on either pulley 512, 513.

Figure 12:
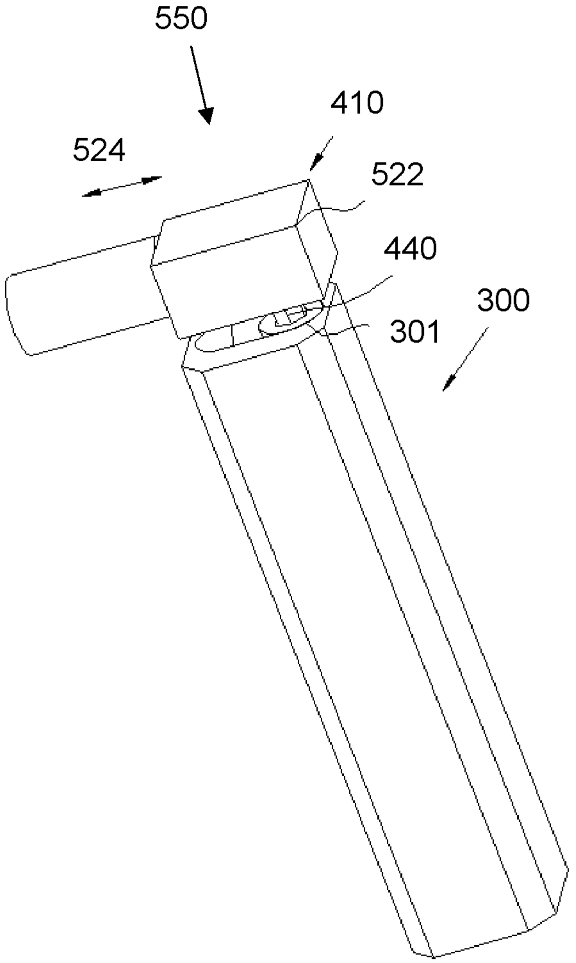
FIG. 12 illustrates a drive assembly coupling a rotor of a progressive cavity pump with a drive motor, according to one arrangement.

An alternative embodiment of a drive assembly 550 is illustrated in FIG. 12. In this arrangement, the progressive cavity pump 300 has a cross sectional shape that is rectangular with beveled corners. This shape is configured to allow the pump 300 to fit into certain housing shapes. The drive motor 410 includes a 90 degree angle gear drive 522 and, as such, the drive motor 410 can be mounted perpendicular to a longitudinal axis of the progressive cavity pump 300. During operation, the drive motor 410 rotates the rotor 301. This rotation causes the rotor 301 to translate along direction 524. The drive motor 410 is moveably disposed within a housing (not shown) that allows the drive motor 410 to translate along the direction 524 with the rotor 301. The drive motor 410 is constrained within its housing in a manner that prevents it from rotating while allowing it to translate. In this arrangement, the drive motor 410 can be directly coupled to the rotor 301 via the output shaft 440. By allowing the motor 410 to translate back and forth within a housing and with the rotor 301, the drive assembly 550 mitigates the use of additional belts and/or couplings to connect the drive motor 410 to the progressive cavity pump 300.

The above arrangements illustrate methods of locating the motor 440 and driving the progressive cavity pump 300 and are not meant to be limiting. In some arrangements, the rotor 301 may be held in a manner that allows it to translate but not rotate, for example, using a stationary pin that passes through a longitudinal axis of the rotor 301 on which the rotor 301 can slide through its translation without rotating. With some arrangements, the rotor 301 can remain stationary and the drive motor 410 rotates the stator 302. One arrangement can use a drive motor with a hollow shaft that is large enough to accept the outer dimensions of the progressive cavity pump 300. In this arrangement, the motor can be mounted coaxially with the stator 302 and drives it directly.

As provided above, the ventilator can operate in two basic control methods, or modes: volume mode and pressure mode. In volume mode, a ventilator can provide inspiration gas to the recipient that produces a specific volume of air with each breath. The volume is generally delivered within a specific inspiration time in order to control the respiratory rate of the recipient. In pressure mode, a ventilator can provide inspiration gas to a recipient in which the inspiratory pressure is controlled.

In one arrangement, the control unit 102 of the ventilator 101 can be configured to control both volume mode and pressure mode of the ventilator. For the positive volumetric ventilator 101, the inspiration volume is determined by the number of rotations of the output shaft 112 of the drive motor 110 and the flow rate is determined by the rotational speed of the output shaft 112 of the drive motor 110. As an example, if a positive displacement pump 103 produces 100 ml of air per revolution of the drive motor 110, an inspiration of 500 ml provides that the pump be driven for five rotations of the output shaft 112. For an inspiration time of one second, output shaft 112 of the drive motor 110 is driven at a rotational speed of 5 rotations per second, or 300 revolutions per minute. As such, the control unit 102 of the ventilator 101 is configured to adjust the number of rotations of the output shaft 112 of the drive motor 110 and the rotational speed of the output shaft 112 of the drive motor 110, as described below.

Figure 13:
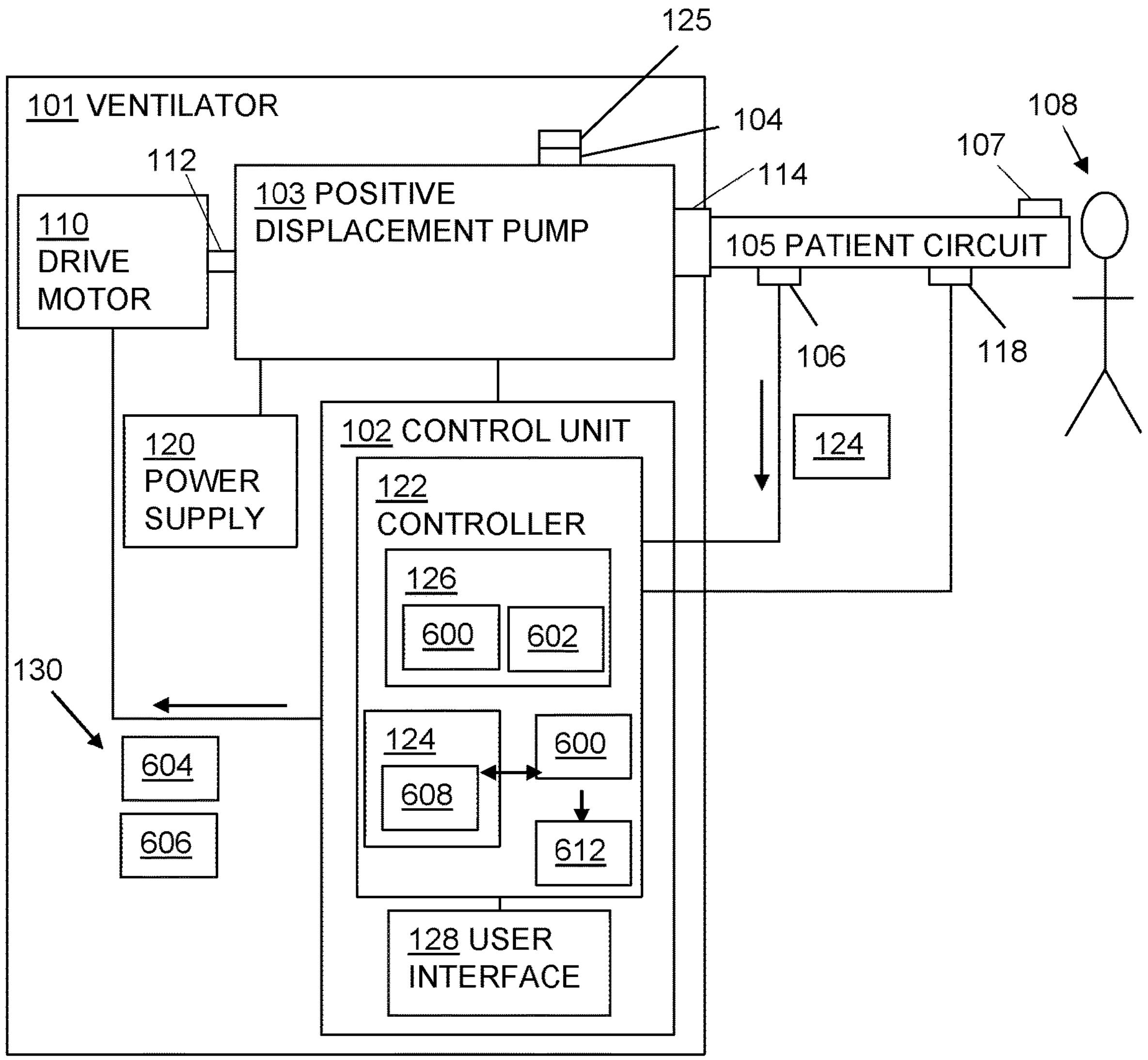
FIG. 13 illustrates operation of a control unit of the ventilator of FIG. 1 in a volume control mode, according to one arrangement.

With reference to FIG. 13, the control unit 102 is configured to control the ventilator 101 in a volume control mode. In one arrangement, termed Mandatory mode, the control unit 102 can initiate the delivery of inspiration gas based on a predetermined inspiration rate and can control both inspiratory and expiratory time. As such, the control unit 102 can be configured to receive an operation signal 126 identifying a target inspiration gas volume value 600 and a target inspiration gas delivery rate value 602 for provision to the recipient 108. For example, it can be determined that the recipient 108 requires an inspiration of 500 ml of inspiration gas (e.g., target inspiration gas volume value 600) in one second at an inspiratory rate of 20 breaths per minute (e.g., target inspiration gas delivery rate value 602). The control unit 102 can receive the values 600, 602 via the operation signal 126 in a variety of ways. In one arrangement, the values 600, 602 provided as part of the operation signal 126 can be selected by a practitioner via the user interface 128 or may be pre-programmed into the controller 122 of the control unit 102.

Following receipt of the operation signal 126, the control unit 102 is configured to transmit, as the drive motor control signal 130, a volume control signal 604 to the drive motor 110 to adjust a number of rotations of the output shaft 112 to correspond with the target inspiration gas volume value 600 and to transmit a velocity control signal 606 to the drive motor 110 to adjust the rotational speed of the output shaft 112 to correspond with the target inspiration gas delivery rate value 602. For example, the control unit 102 can transmit a volume control signal 604 to the drive motor 110 to adjust the number of rotations of the output shaft 112 such that the ventilator 101 delivers 500 ml of inspiration gas. Further the control unit 102 can transmit a velocity control signal 606 to the drive motor 110 to adjust the rotational velocity of the output shaft 112 such that the ventilator 101 provides the 500 ml of inspiration gas in a period of one second. The control unit 102 then ceases drive to allow for expiration. To achieve an inspiratory rate of 20 breaths per minute, the control unit 102 provides a one second inspiration followed by a two second expiration in an alternating manner.

In one arrangement, termed Assist-Control mode, the control unit 102 can initiate the delivery of inspiration gas based on detection of the recipient 108 initiating an inspiration. For example, the control unit 102 is configured to receive a pressure sensor signal 124 from the pressure sensor 106 that identifies the recipient's initial inspiratory pressure. During operation, as the recipient 108 attempts to inhale, the action causes the inspiratory pressure to decrease. The pressure sensor 106 detects this pressure drop and forwards the corresponding pressure sensor signal 124 to the control unit 102.

In response to receiving the pressure sensor signal 124, the control unit 102 compares a pressure value 608 of the pressure sensor signal 124 to a baseline pressure value 610. For example, the baseline pressure value 610 can be preset as equivalent to the patient lung pressure at an expired state. In response to detecting an inspiratory pressure decrease 612 between the pressure value 608 and the baseline pressure value 610, the control unit 102 can transmit the volume control signal 604 to the drive motor 110 to adjust the number of rotations of the output shaft 112 to correspond to the target inspiration gas volume value 600 and to transmit the velocity control signal 606 to the drive motor 110 to adjust the rotational speed of the output shaft 112 to correspond to the target inspiration gas delivery rate value 602. Delivery of the volume control signal 604 and velocity control signal 606 causes the drive motor 110 to trigger the delivery of inspiration gas to the recipient 108 in order to help the recipient 108 breathe.

If the recipient 108 does not attempt an inspiration on their own within a predetermined amount of time, the ventilator 101 can initiate an inspiration, as it does in Mandatory mode. In the above scenarios, the flow rate and duration are controlled by the control unit 102 and the inspiratory pressure is a result of the flow rate.

Figure 14:
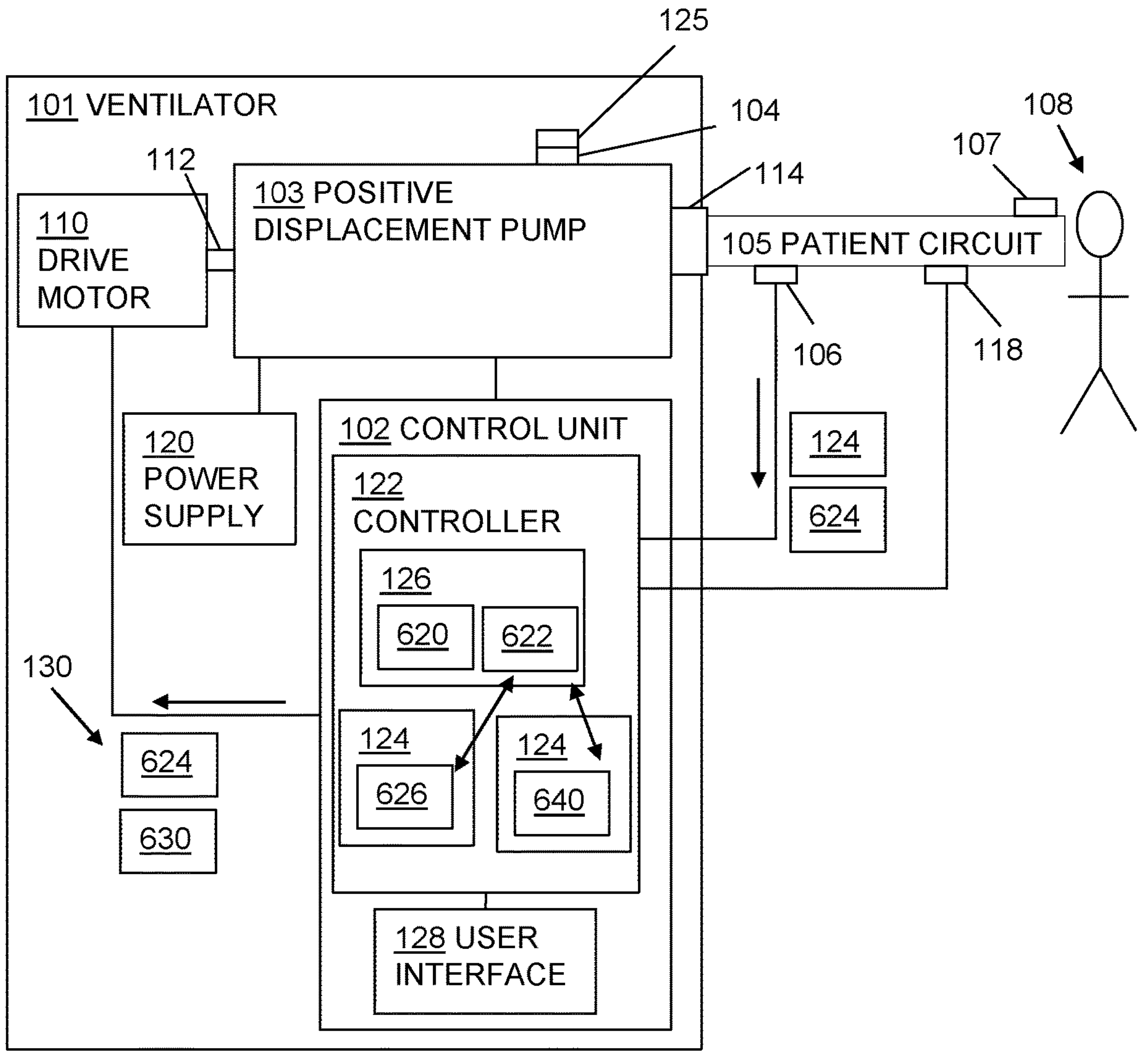
FIG. 14 illustrates operation of a control unit of the ventilator of FIG. 1 in a pressure control mode, according to one arrangement.

With reference to FIG. 14, the control unit 102 is configured to control the ventilator 101 in a pressure control mode such that when an inspiration is triggered, the control unit 102 begins driving the pump 103 and the pressure sensor 106 senses the inspiratory pressure. In one arrangement, termed Mandatory mode, the control unit 102 can initiate the delivery of inspiration gas based on a predetermined inspiratory pressure. As such, the control unit 102 can be configured to receive an operation signal 126 identifying an initial inspiration gas delivery rate 620 and a target inspiratory pressure value 622 for provision to a recipient 108. For example, the operation signal 126 can identify the initial inspiration gas delivery rate 620 as the rotational speed of the output shaft 112 of the drive motor 110 and the target inspiratory pressure value 622 as being 40 cm $H_2O$.

Following receipt of the operation signal 126, the control unit 102 is configured to transmit a velocity control signal 624 to the drive motor 110 to set the rotational speed of the output shaft 112 to correspond to the initial inspiration gas delivery rate 620. As such, in this example, the control unit 102 can transmit the velocity control signal 624 to cause the output shaft 112 to rotate at a rate sufficient to provide the target inspiratory pressure to the recipient 108.

In response to transmission of the velocity control signal 624, the control unit 102 is configured to receive a pressure sensor signal 124 from the pressure sensor 106 where the pressure sensor signal 124 identifies a recipient inspiratory pressure value 626. The control unit 102 is configured to then compare the recipient inspiratory pressure value 626 with the target inspiratory pressure value 622. When the recipient inspiratory pressure value 626 is unequal to the target inspiratory pressure value 622 the control unit 102 is configured to transmit an adjusted velocity control signal 630 to the drive motor 110 to adjust the rotational speed of the output shaft 112. For example, assume the case where the recipient inspiratory pressure value 626 is below the target inspiratory pressure value 622 of 40 cm $H_2O$. In such a case, the control unit 102 can transmit an adjusted velocity control signal 630 to increase the drive speed of the output shaft 112 until an updated pressure sensor signal 124 received from the pressure sensor 106 identifies the target pressure of 40 cm $H_2O$ is reached for the duration of the inspiration. Conversely, assume the case where the recipient inspiratory pressure value 626 is above the target inspiratory pressure value 622 of 40 cm $H_2O$. In such a case, the control unit 102 can transmit an adjusted velocity control signal 630 to decrease the drive speed of the output shaft 112 until an updated pressure sensor signal 124 received from the pressure sensor 106 identifies the target pressure of 40 cm $H_2O$ is reached for the duration of the inspiration.

In one arrangement, termed Assist-Control mode, the control unit 102 can initiate the delivery of inspiration gas based on detection of the recipient 108 initiating an inspiration. For example, the control unit 102 is configured to receive a pressure sensor signal 124 from the pressure sensor 106 that identifies the recipient's initial inspiratory pressure. During operation, as the recipient 108 attempts to inhale, the action causes the inspiratory pressure to decrease. The pressure sensor 106 detects this pressure drop and forwards the corresponding initial inspiratory pressure to the control unit 102 as an initial inspiratory pressure value 640 of the pressure sensor signal 124.

Next the control unit 102 is configured to compare the initial inspiratory pressure value 640 of the pressure sensor signal 124 to a baseline pressure value 622. In response to detecting the pressure value 626 identifying an inspiratory pressure decrease relative to the baseline pressure value 622, the control unit 102 is configured to transmit a velocity control signal 624 to the drive motor 110 to set the rotational speed of the output shaft 112 to correspond to the initial inspiration gas delivery rate 620. As such, in this example, the control unit 102 can transmit the velocity control signal 624 to cause the output shaft 112 to rotate at a rate sufficient to provide the target pressure to the recipient 108.

In response to transmission of the velocity control signal 624, the control unit 102 is configured to receive an updated pressure sensor signal 624 from the pressure sensor 106 where the pressure sensor signal 624 identifies a recipient inspiratory pressure value 626. The control unit 102 can them compare the recipient inspiratory pressure value 626 with the target inspiratory pressure value 622. When the control unit 102 detects the recipient inspiratory pressure value 626 as being unequal to the target inspiratory pressure value 622, the control unit 102 transmits an adjusted velocity control signal 630 to the drive motor 110 to adjust the rotational speed of the output shaft 112. As such, the target pressure is maintained for the duration of the inspiration. In some arrangements, the controlled pressure may be variable, following a pressure profile.

In one arrangement, the control unit 102 is configured to control the ventilator 101 in a continuous pressure control mode, such as utilized when the ventilator 101 provides continuous positive airway pressure (CPAP) to a recipient 108.

Figure 15:
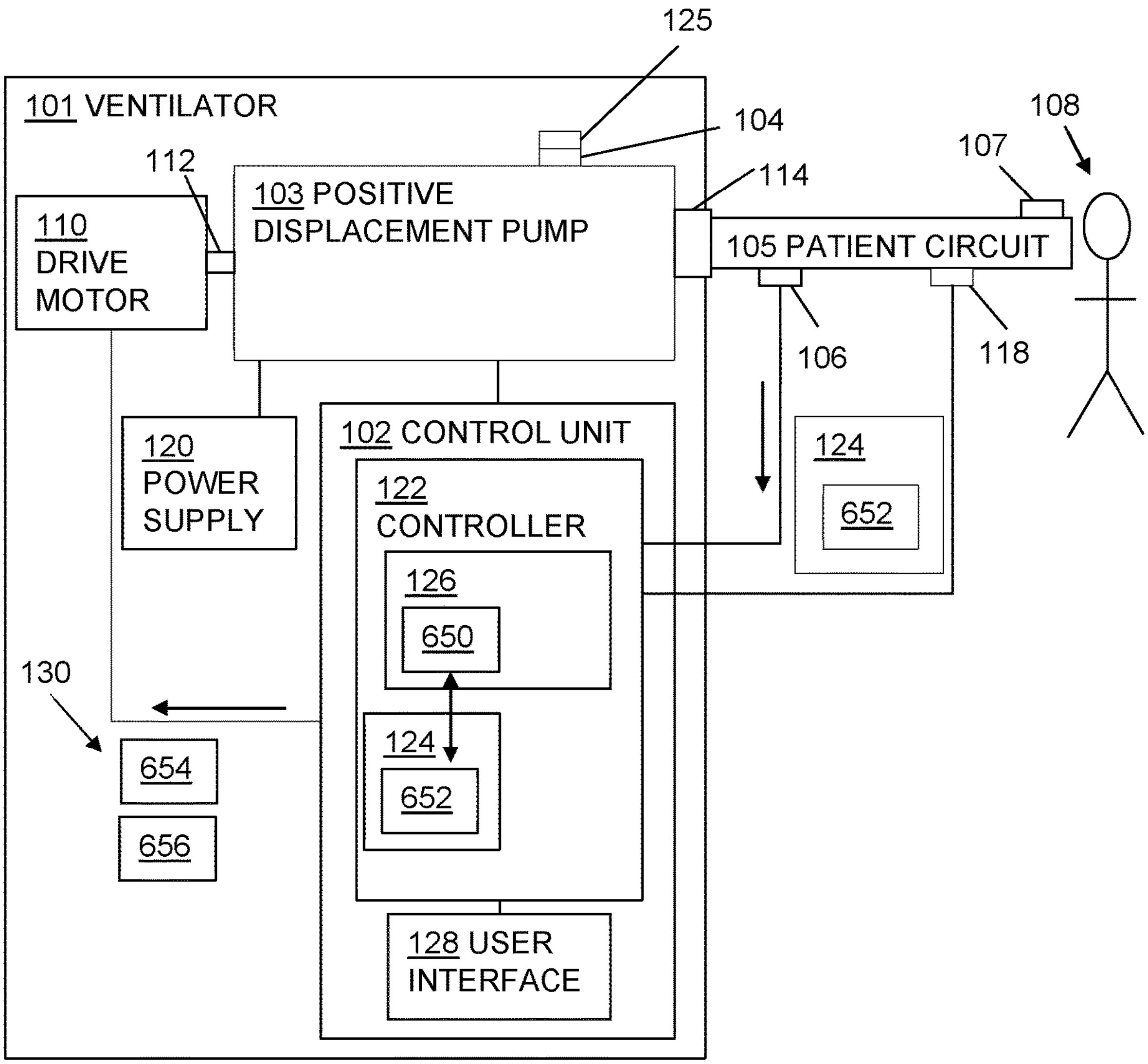
FIG. 15 illustrates operation of a control unit of the ventilator of FIG. 1 in a continuous positive airway pressure mode, according to one arrangement.

With reference to FIG. 15, the control unit 102 receives an operation signal 126 identifying a constant inspiration gas pressure value 650 for provision to a recipient 108. The control unit 102 can then receive a pressure sensor signal 124 from the pressure sensor 106 that identifies the recipient's gas pressure. For example, the pressure sensor signal 124 can identify a pressure value 652 associated with the recipient's inspiration or expiration pressure taken at any point during a breathing cycle.

In response to receiving the pressure signal 124, the control unit 102 is configured to compare the pressure value 652 of the pressure sensor signal 124 to the constant inspiration gas pressure value 650. In response to detecting a pressure decrease between the pressure value 652 and the constant inspiration gas pressure value 650 the control unit 102 is configured to transmit a velocity control signal 654 to the drive motor 110 to increase the rotational speed of the output shaft 112. For example, the pressure decrease may indicate the recipient 108 is inhaling. As such, by increasing the rotational speed of the output shaft 112, the control unit can increase the pressure of inspiration gas delivered to the recipient 108. In response to detecting a pressure increase between the pressure value 652 and the constant inspiration gas pressure value 650, the control unit 102 is configured to transmit a velocity control signal 656 to the drive motor 110 to decrease the rotational speed of the output shaft 112. For example, the pressure increase may indicate the recipient 108 is exhaling. As such, by decreasing the rotational speed of the output shaft 112, the control unit can decrease the pressure of inspiration gas delivered to the recipient 108.

The ventilator 101 can be configured to operate in a variety of other modes as well. In dual modes, both pressure and volume may be controlled. For example, in Pressure Regulated Volume Control (PRVC) a volume target backup is added to a pressure assist-control mode. The ventilator 101 can be configured to operate interactive modes, adaptive modes, high frequency oscillation modes, and others. The ventilator 101 can be configured to operate with a high flow nasal catheter. By changing the configuration of the control unit, all of these modes can be accomplished by the current innovation with the use of the positive volumetric ventilation system 100.

While various embodiments of the innovation have been particularly shown and described, it will be understood by those skilled in the art that various changes in form and details may be made therein without departing from the spirit and scope of the innovation as defined by the appended claims.

What is claimed is:

1. A ventilator, comprising:

a positive displacement pump having a drive motor and configured to output a predetermined volume of inspiratory gas for each rotation of an output shaft of the drive motor; and a control unit having a controller comprising a memory and a processor, the control unit disposed in electrical communication with the drive motor, the controller configured to:

receive an operation signal identifying a target inspiration gas volume value and a target inspiration gas delivery rate value for provision to a recipient, and transmit a drive motor control signal to the drive motor to adjust a number of rotations of the output shaft based upon the operation signal to control inspiratory gas volume; wherein when transmitting the drive motor control signal to the drive motor, the controller is configured to:

transmit a volume control signal to the drive motor to adjust the number of rotations of the output shaft to correspond to the target inspiration gas volume value based upon the predetermined volume of inspiratory gas delivered by the positive displacement pump for each rotation of the output shaft, and transmit a velocity control signal to the drive motor to adjust the rotational speed of the output shaft to correspond to the target inspiration gas delivery rate value.

2. The ventilator of claim 1, wherein when receiving the operation signal, the controller is further configured to:

receive a pressure sensor signal from a pressure sensor, the pressure sensor signal identifying an initial inspiratory pressure of the recipient;

compare a pressure value of the pressure sensor signal to a baseline pressure value; and in response to detecting an inspiratory pressure decrease between the pressure value of the pressure sensor signal and the baseline pressure value, transmit the volume control signal to the drive motor to adjust the number of rotations of the output shaft to correspond to the target inspiration gas volume value and transmit the velocity control signal to the drive motor to adjust the rotational speed of the output shaft to correspond to the target inspiration gas delivery rate value.

3. The ventilator of claim 1, wherein:

when receiving the operation signal, the controller is configured to receive the operation signal identifying an initial inspiration gas delivery rate and a target inspiratory pressure value for provision to the recipient; and when transmitting the drive motor control signal to the drive motor, the controller is configured to:

transmit a velocity control signal to the drive motor to set the rotational speed of the output shaft to correspond to the initial inspiration gas delivery rate, receive a pressure sensor signal from a pressure sensor, the pressure sensor signal identifying a recipient inspiratory pressure value, compare the recipient inspiratory pressure value with the target inspiratory pressure value, and when the recipient inspiratory pressure value is unequal to the target inspiratory pressure value, transmit an adjusted velocity control signal to the drive motor to adjust the rotational speed of the output shaft.

4. The ventilator of claim 3, wherein when receiving the pressure sensor signal, the controller is further configured to:

receive the pressure sensor signal from the pressure sensor, the pressure sensor signal identifying an initial inspiratory pressure of the recipient;

compare an initial inspiratory pressure value of the pressure sensor signal to a baseline pressure value; and in response to detecting the pressure value identifying an inspiratory pressure decrease relative to the baseline pressure value:

transmit the velocity control signal to the drive motor to set the rotational speed of the output shaft to correspond to the initial inspiration gas delivery rate, receive an updated pressure sensor signal from the pressure sensor, the updated pressure sensor signal identifying an updated recipient inspiratory pressure value, compare the updated recipient inspiratory pressure value from the updated pressure sensor signal with the target inspiratory pressure value, and when the updated recipient inspiratory pressure value from the updated pressure sensor signal is unequal to the target inspiratory pressure value, transmit the adjusted velocity control signal to the drive motor to adjust the rotational speed of the output shaft.

5. The ventilator of claim 1, wherein, the controller is configured to:

when receiving the operation signal, receive the operation signal identifying a constant inspiration gas pressure value for provision to the recipient;

receive a pressure sensor signal from a pressure sensor, the pressure sensor signal identifying a gas pressure of the recipient;

compare a pressure value of the pressure sensor signal to the constant inspiration gas pressure value;

in response to detecting a pressure decrease between the pressure value of the pressure sensor signal and the constant inspiration gas pressure value, transmit the velocity control signal to the drive motor to increase the rotational speed of the output shaft; and in response to detecting a pressure increase between the pressure value of the pressure sensor signal and the constant inspiration gas pressure value, transmit the velocity control signal to the drive motor to decrease the rotational speed of the output shaft.

6. The ventilator of claim 1, wherein the positive displacement pump is configured as a reciprocating pump.

7. The ventilator of claim 1, wherein the positive displacement pump is configured as a progressive cavity pump.

8. The ventilator of claim 1, further comprising a selector device disposed in fluid communication with the positive displacement pump, the selector device configured to allow flow of at least one of air and oxygen into the positive displacement pump.

9. The ventilator of claim 8, further comprising an oxygen sensor disposed in fluid communication with the inspiratory gas, the oxygen sensor configured to measure a percentage of oxygen within the inspiration gas provided by the positive displacement pump.

10. In a ventilator, a method of providing an inspiration gas to a recipient, comprising:

receiving an operation signal identifying a target inspiration gas volume value and a target inspiration gas delivery rate value for provision to the recipient; and transmitting a drive motor control signal to a drive motor of the ventilator to adjust a number of rotations of an output shaft based upon the operation signal to control inspiratory gas volume, wherein transmitting the drive motor control signal to the drive motor comprises:

transmitting a volume control signal to the drive motor to adjust the of rotations of the output shaft to correspond to the target inspiration gas volume value based upon a predetermined volume of inspiratory gas delivered by a positive displacement pump for each rotation of the output shaft, and transmitting a velocity control signal to the drive motor to adjust the rotational speed of the output shaft to correspond to the target inspiration gas delivery rate value.

11. The method of claim 10, comprising:

receiving a pressure sensor signal from a pressure sensor, the pressure sensor signal identifying an initial inspiratory pressure of the recipient;

comparing a pressure value of the pressure sensor signal to a baseline pressure value; and in response to detecting an inspiratory pressure decrease between the pressure value of the pressure sensor signal and the baseline pressure value, transmit the volume control signal to the drive motor to adjust the number of rotations of the output shaft to correspond to the target inspiration gas volume value and transmit the velocity control signal to the drive motor to adjust the rotational speed of the output shaft to correspond to the target inspiration gas delivery rate value.

12. The method of claim 10, wherein:

receiving the operation signal comprises receiving the operation signal identifying an initial inspiration gas delivery rate and a target inspiratory pressure value for provision to the recipient; and transmitting the drive motor control signal to the drive motor comprises:

transmitting a velocity control signal to the drive motor to set the rotational speed of the output shaft to correspond to the initial inspiration gas delivery rate, receiving a pressure sensor signal from a pressure sensor, the pressure sensor signal identifying a recipient inspiratory pressure value, comparing the recipient inspiratory pressure value with the target inspiratory pressure value, and when the recipient inspiratory pressure value is unequal to the target inspiratory pressure value, transmitting an adjusted velocity control signal to the drive motor to adjust the rotational speed of the output shaft.

13. The method of claim 12, wherein receiving the pressure sensor signal comprises:

receiving the pressure sensor signal from the pressure sensor, the pressure sensor signal identifying an initial inspiratory pressure of the recipient;

comparing an initial inspiratory pressure value of the pressure sensor signal to a baseline pressure value; and in response to detecting the pressure value identifying an inspiratory pressure decrease relative to the baseline pressure value:

transmitting the velocity control signal to the drive motor to set rotational speed of the output shaft to correspond to the initial inspiration gas delivery rate, receiving an updated pressure sensor signal from the pressure sensor, the updated pressure sensor signal identifying an updated recipient inspiratory pressure value, comparing the updated recipient inspiratory pressure value from the updated pressure sensor signal with the target inspiratory pressure value, and when the updated recipient inspiratory pressure value from the updated pressure sensor signal is unequal to the target inspiratory pressure value, transmitting the adjusted velocity control signal to the drive motor to adjust the rotational speed of the output shaft.

14. The method of claim 10, wherein:

receiving the operation signal comprises: receiving the operation signal identifying a constant inspiration gas pressure value for provision to the recipient;

receiving a pressure sensor signal from a pressure sensor, the pressure sensor signal identifying a gas pressure of the recipient;

comparing a pressure value of the pressure sensor signal to the constant inspiration gas pressure value;

in response to detecting a pressure decrease between the pressure value of the pressure sensor signal and the constant inspiration gas pressure value, transmitting the velocity control signal to the drive motor to increase the rotational speed of the output shaft; and in response to detecting a pressure increase between the pressure value of the pressure sensor signal and the constant inspiration gas pressure value, transmitting the velocity control signal to the drive motor to decrease the rotational speed of the output shaft.

15. A ventilator system, comprising:

a ventilator, comprising:

a positive displacement pump having a drive motor and configured to output a predetermined volume of inspiratory gas for each rotation of an output shaft of the drive motor, and a control unit having a controller comprising a memory and a processor, the control unit disposed in electrical communication with the drive motor, the controller configured to:

receive an operation signal identifying a target inspiration gas volume value and a target inspiration gas delivery rate value for provision to a recipient, and transmit a drive motor control signal to the drive motor to adjust number of rotations of the output shaft based upon the operation signal to control inspiratory gas volume, wherein when transmitting the drive motor control signal to the drive motor, the controller is configured to transmit a volume control signal to the drive motor to adjust the number of rotations of the output shaft to correspond to the target inspiration gas volume value based upon the predetermined volume of inspiratory gas delivered by the positive displacement pump for each rotation of the output shaft, and transmit a velocity control signal to the drive motor to adjust the rotational speed of the output shaft to correspond to the target inspiration gas delivery rate value; and a patient circuit disposed in fluid communication with the ventilator, the patient circuit configured to direct inspiration gas from the ventilator toward the recipient.

16. The ventilator system of claim 15, wherein:

when receiving the operation signal, the controller is configured to receive the operation signal identifying an initial inspiration gas delivery rate and a target inspiratory pressure value for provision to the recipient; and when transmitting the drive motor control signal to the drive motor, the controller is configured to:

transmit a velocity control signal to the drive motor to set the rotational speed of the output shaft to correspond to the initial inspiration gas delivery rate, receive a pressure sensor signal from a pressure sensor, the pressure sensor signal identifying a recipient inspiratory pressure value, compare the recipient inspiratory pressure value with the target inspiratory pressure value, and when the recipient inspiratory pressure value is unequal to the target inspiratory pressure value, transmit an adjusted velocity control signal to the drive motor to adjust the rotational speed of the output shaft.

17. The ventilator system of claim 15, wherein the controller is configured to:

when receiving the operation signal, receive the operation signal identifying a constant inspiration gas pressure value for provision to the recipient;

receive a pressure sensor signal from a pressure sensor, the pressure sensor signal identifying a gas pressure of the recipient;

compare a pressure value of the pressure sensor signal to the constant inspiration gas pressure value;

in response to detecting a pressure decrease between the pressure value and the constant inspiration gas pressure value, transmit the velocity control signal to the drive motor to increase the rotational speed of the output shaft; and in response to detecting a pressure increase between the pressure value and the constant inspiration gas pressure value, transmit the velocity control signal to the drive motor to decrease the rotational speed of the output shaft.

* * * * *